US005980886A

United States Patent [19]
Kay et al.

[11] Patent Number: 5,980,886
[45] Date of Patent: Nov. 9, 1999

[54] RECOMBINANT VECTORS FOR RECONSTITUTION OF LIVER

[75] Inventors: Mark A. Kay; Andre Lieber, both of Seattle, Wash.

[73] Assignee: University of Washington, Seattle, Wash.

[21] Appl. No.: 08/819,377

[22] Filed: Mar. 17, 1997

Related U.S. Application Data

[63] Continuation of application No. 08/476,257, Jun. 7, 1995, abandoned, which is a continuation-in-part of application No. 08/357,508, Dec. 14, 1994, abandoned.

[51] Int. Cl.$^6$ .............................. A01N 63/00; A01N 43/04
[52] U.S. Cl. ........................ 424/93.21; 514/44; 424/93.1; 424/93.2
[58] Field of Search ........................... 514/44; 424/93.21; 435/172.3, 320.1, 325; 530/384

[56] References Cited

U.S. PATENT DOCUMENTS

| | | | |
|---|---|---|---|
| 4,861,719 | 8/1989 | Miller ...................................... | 435/236 |
| 5,124,263 | 6/1992 | Temin et al. ............................. | 435/349 |
| 5,219,740 | 6/1993 | Miller et al. ............................ | 435/69.6 |
| 5,399,346 | 3/1995 | Anderson et al. .................... | 424/93.21 |

FOREIGN PATENT DOCUMENTS

| | | |
|---|---|---|
| WO 92/12242 | 7/1992 | WIPO . |
| WO 94/02601 | 2/1994 | WIPO . |
| WO 94/27556 | 12/1994 | WIPO . |

OTHER PUBLICATIONS

Brown, D. "Gene Therapy "Oversold"By Researchers, Journalists", The Washington Post (Dec. 8, 1995), pp. A1, A22.
Ledley, F. "Hepatic Gene Therapy : Present and Future", Hepatology : 18(5) : 1263–1273 (1993).
Lieber, A. et al. "A Modified Urokinase . . . " Human Gene Therapy 6: 1029–37 (1995).
Marshall, E. "Gene Therapy's Growing Pains" Science 269 :1050–1055 (1995).
Rhim, JA et al. "Replacement of Diseased Mouse Liver by Hepatic Cell Transplantation" Science 263: 1149–1152 (1994).
George et al., "Ribozyme Mediated Cleavage of Hepatitis B Virus Surface Antigen mRNA," J. Cell. Biochem. Suppl. 17E:212, abs. S407 (1993).
Shih et al., "A Novel Clamp–Like Structure Enables Retargeting of a Ribozyme Derived from the Antigenome of Hepatitis Delta Virus and Trans–Cleavage of Heterologous RNA," J. Cell. Biochem. 17E:214, abs. S416 (1993).
Fausto, "Hepatocyte Differentiation and Liver Progenitor Cells," Curr. Op. Cell Biol. 2:1036–1042 (1990).
George et al., "Ribozyme Mediated Cleavage of Hepatitis B Virus Surface Antigen mRNA," J. Cell. Biochem. Suppl. 17E:212, abs S407 (1993).
Gorlich et al., "A Protein of the Endoplasmic Reticulum Involved Early in Polypeptide Translocation," Nature 357:47–52 (1992).

Graham and Prevec, "Manipulation of Adenovirus Vectors," Methods in Molecular Biology: Gene Transfer and Expression Protocols, The Humana Press 7:109–128 (1991).
Grundmann et al., Liver Regeneration After Experimental Injury Lesch & Reuter (eds.), NY: Stratton Intercontinental Medical Book Co. (1973).
Heckel et al., "Neonatal Bleeding in Transgenic Mice Expressing Urokinase–Type Plasminogen Activator," Cell 62:447–456 (1990).
Kay et al., "Hepatic Gene Therapy: Persistent Expression of Human α1–Antitrypsin in Mice after Direct Gene Delivery In Vivo," Hum. Gene Ther. 3:641–647 (1992).
Kay et al., "In vivo Hepatic Gene Therapy: Complete Albeit Transient Correction of Factor IX Deficiency in Hemophilia B Dogs," Proc. Natl. Acad. Sci. USA 91:2353–2357 (1994).
Kay et al., "In Vivo Gene Therapy of Hemophilia B: Sustained Partial Correction in Factor IX–Deficient Dogs," Sci. 262:117–119 (1993).
Ledley et al., "Hepatic Gene Therapy: Present and Future," Hepatol. 18 (5) :1263–1273 (1993).
Li et al., "Assessment of Recombinant Adenoviral Vectors for Hepatic Gener Therapy," Human Gene Ther. 4:403–409 (1993).
Miller, "Progress Toward Human Gene Therapy," Blood 76:271–278 (1990).
Miller et al., "Gene Transfer by Retrovirus Vectors Occurs Only in Cells That are Actively Replicating at the Time of Infection," Mol. Cell. Biol. 10:4329–4342 (1990).
Miller, "Human Gene Therapy Comes of Age," Nature 357:455–460 (1992).
Nagai et al., "Molecular Cloning of cDNA Coding for Human Preprourokinase," Gene 36:183–188 (1985).
Pelham, "Evidence that Luminal ER Proteins are Sorted From Secreted Proteins in a Post–ER Compartment," EMBO J. 7:913–918 (1988).
Rhim et al., "Replacement of Diseased Mouse Liver by Hepatic Cell Transplantation," Sci. 563:1149–1152 (1994).
Sandgren et al., "Complete Hepatic Regeneration After Somatic Deletion of an Albumin–Plasminogen Activator Transgene," Cell 66:245–256 (1991).
Schutze et al., "An N–terminal Double–Arginine Motif Maintains Type II Membrane Proteins in the Endoplasmic Reticulum," EMBO J. 13:1696–1705 (1994).

(List continued on next page.)

Primary Examiner—Brian R. Stanton
Assistant Examiner—Deborah J. R. Clark
Attorney, Agent, or Firm—Campbell & Flores

[57] ABSTRACT

A combination of retroviral and adenoviral vectors are used for high efficiency gene transfer into hepatocytes, resulting in long term gene expression. Hepatocytes are transduced in vivo with a recombinant adenovirus vector that expresses a molecule capable of inducing hepatocyte regeneration, such as urokinase plasminogen activator (uPA) or tissue plasminogen activator (tPA), resulting in a high rate of liver regeneration. During the regenerative phase, ex vivo or in vivo retroviral-mediated gene transfer into hepatocytes results in greater transduction efficiencies. The compositions and methods thus provide new means for gene therapy, and transgenic non-human animals useful in developing new therapeutic and preventative agents.

13 Claims, 8 Drawing Sheets

OTHER PUBLICATIONS

Shih et al., "A Novel Clamp–Like Structure Enables Retargeting of a Ribozyme Derived from the Antigenome of Hepatitis Delta Virus and Trans–Cleavage of Heterologous RNA" *J. Cell. Bichem.* 17E:214, abs S416 (1993).

Stratford–Perricaudet et al., "Widespread Long–term Gene Transfer to Mouse Skeletal Muscles and Heart," *J. Clin. Invest.* 90:626–630 (1992).

Strubin et al., "Two Forms of the Ia Antigen–Associated Invariant Chain Result from Alternative Initiations at Two In–Phase AUGs," *Cell* 47:619–625 (1986).

Yang et al., "Cellular Immunity to Viral Antigens Limits E1–deleted Adenoviruses for Gene Therapy," *Proc. Natl. Acad. Sci. USA* 91:4407–4411 (1994).

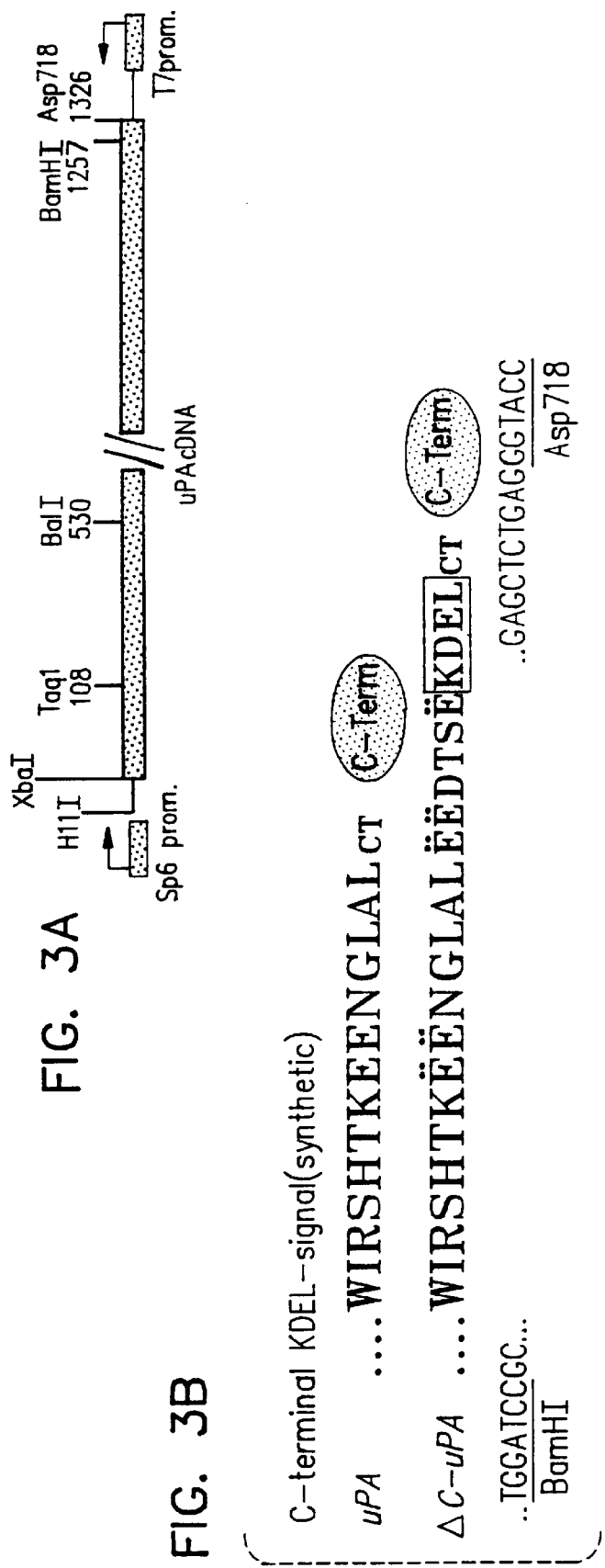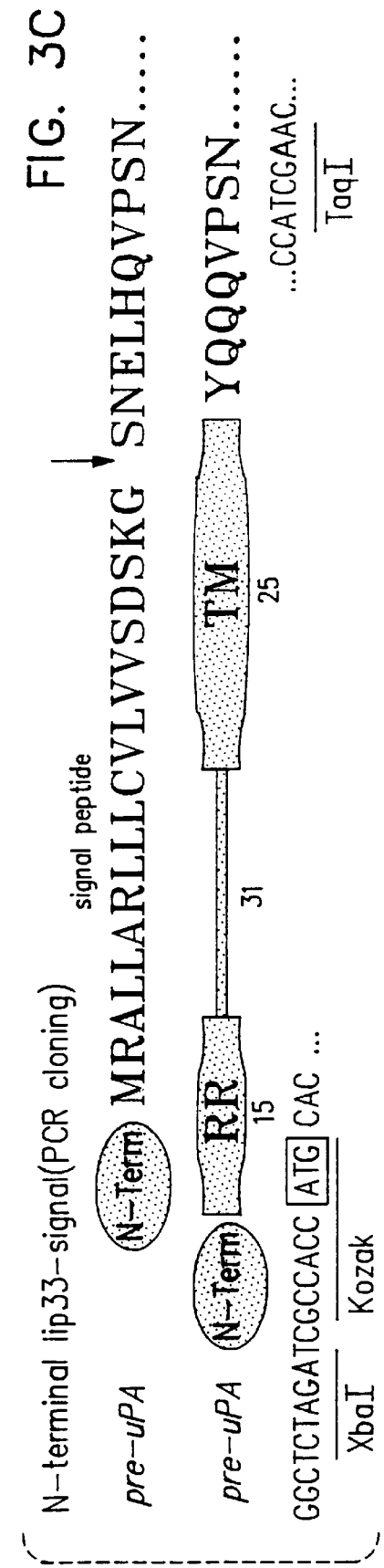

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GATCCCGCAG TCACACCAAG GAAGAGAATG GCCTGGCCCC TC      42

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

GAAGAAGATA CCTCTGAAAA AGATGAGCTC TGAGG      35

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

-continued

```
TCTTCCTTGG TGTGACTGCG                                                          20

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CAGAGGTATC TTCGAGGGCC AGGCCATTC                                                29

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GTACCCTCAG AGCTCATCTT TTT                                                      23

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGCTCTAGAT CGCCACCATG CACAGGAGGA GAAGCAGGAG C                                  41

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GTTCGATGGA ACCTGCTGCT GCTACAGGAA GTAGGC                                        36
```

RECOMBINANT VECTORS FOR RECONSTITUTION OF LIVER

This application is a continuation of application Ser. No. 08/476,257, filed Jun. 7, 1995, now abandoned, which is a continuation-in-part of application Ser. No. 08/357,508, filed Dec. 14, 1994, now abandoned.

GOVERNMENT SUPPORT

Certain embodiments of the invention described herein were made in the course of work supported by the National Institutes of Health pursuant to grant no. DK47754. Therefore, the U.S. Government has certain rights in this invention.

BACKGROUND OF THE INVENTION

Gene therapy involves the introduction of genetic material into the cells of an organism to treat or prevent a disease. The material transferred can be from one to a few genes in size. Since many hereditary diseases are caused by defects in single genes, there are many potential applications of this technique to the treatment of disease in humans and other animals. In addition, gene therapy is useful in the treatment and prevention of acquired diseases, such as infectious diseases and cancer.

Gene therapy can be directed to either an animal's germ line or somatic cells. For ethical and practical considerations, only somatic cell therapy is being pursued for humans. A variety of cell types have been targeted in somatic cell gene therapy systems, including hematopoietic cells, skin fibroblasts and keratinocytes, hepatocytes, endothelial cells, skeletal and smooth muscle cells, and lymphocytes, each with varying success.

The hematopoietic stem cells are a primary target for gene therapy because of well developed procedures for bone marrow transplantation, the many types and wide distribution of hematopoietic cells, and the existence of many diseases that affect hematopoietic cells. However, hematopoietic stem cells have proven difficult to infect in sufficient numbers with gene vectors, and differentiated hematopoietic cells suffer from short term expression of the gene of interest. Miller, *Blood* 76: 271–278 (1990), and Miller, *Nature* 357: 455–460 (1992). Gene transfer methods into muscle cells also demonstrate relatively short term expression and/or expression at low levels, and do not allow for efficient transport of the gene product into the bloodstream. Vascular endothelial cells have the advantage of direct access to the circulation, but are limited by the number of endothelial cells present in large vessels, since the layer of endothelial cells that line the vessels is only one cell thick. Gene transfer into lymphocytes is limited by the finite lifespan of the cells and thus requires repetitive administration to treat an ongoing disease. Gene transfer experiments into skin fibroblasts and keratinocytes have also been hampered by lack of prolonged improvement or insufficient levels of expressions.

Methods for gene therapy involving the liver have relied on gene transfer ex vivo, i.e., into hepatocytes which have been removed from a patient and are then reimplanted into the liver, or gene transfer in vivo, i.e., gene transfer directly into the liver. For ex vivo methods, gene transfer into cells must occur at high efficiency to obtain suitable numbers of cells for transplantation, because primary cultures of hepatocytes cannot be expanded.

Using the ex vivo approach, long term gene expression from transduced hepatocytes has been accomplished with retroviral vectors. The efficiency of transduction is relatively low, however, and the protein may not be expressed in therapeutically or prophylactically effective amounts. In one ex vivo method approximately 20% of a patient's liver is surgically removed, the cells are then transduced with the retroviral vector, and then implanted back into the patient. The retrovirus has been shown to infect only dividing cells. Miller et al., *Mol. Cell. Biol.* 10:4239–4242 (1990). This approach suffers from obvious disadvantages of surgical procedures and a low efficiency of transduction and expression of the gene product of interest.

The direct in vivo approach involves performing a two-thirds partial hepatectomy followed by portal vein infusion of the vector. The removal of the majority of the liver is needed to stimulate liver regeneration so that the retrovirus will integrate into the cell's chromosome. As with the ex vivo approach, this method suffers from requiring a major surgical procedure and under the best of conditions only about 1% of the liver mass contains the genetically modified vectors.

As an alternative to retroviral-mediated hepatic gene therapy, the adenovirus presents a transfer vector that can infect nonreplicating cells at high efficiency. Unfortunately, adenoviral DNA remains extra-chromosomal and thus is slowly lost from transduced hepatocytes over a period of several months. Li et al., *Human Gene Ther.* 4: 403–409 (1993); Kay et al., *Proc. Natl. Acad. Sci.USA* 91: 2353–2357 (1994). Additionally, a substantial portion of the adenovirus is taken up by organs and tissues other than the liver, which may raise issues of safety. (Smith et al., 1993 and Kay et al., ibid.). And, as adenovirus stimulates the production of neutralizing antibodies in an infected host, patients who have been naturally infected with adenovirus may be resistant to gene therapy using this vector, or secondary transductions may be prevented by the presence of antibodies produced in response to a primary transduction. (Smith ibid., Kay, ibid.).

The liver is a desirable target for somatic gene transfer because it is a large organ that is responsible for the synthesis, processing and secretion of many circulating proteins, including many of the plasma coagulation proteins. Because of the liver's involvement in many diseases of medical importance much effort has focused on replacing diseased livers by transplantation or, due to a severe shortage of donor livers, by implantation of healthy liver cells. Typically, however, implanted hepatocytes have made only small and temporary contributions to liver function.

Transgenic animal technology has been employed to create and analyze models of diseases affecting many organs, including the liver. A variety of transgenes have been reported to be associated with liver lesions, including urokinase-type plasminogen activator (uPA). In mice containing a albumin-urokinase transgene the hepatocyte-targeted expression of the uPA gene created a functional liver deficit. The uPA gene caused the fatal hemorrhaging of newborn mice, and survivors displayed hypofibrinogenemia and unclottable blood. It was thus concluded that any injury sufficient to initiate bleeding was rapidly fatal in affected mice. Heckel et al., *Cell* 62: 447–456 (1990). Surviving mice did show a gradual decrease in the level of plasma uPA activity, accompanied by a restoration of clotting function within one to two months. This was explained by a report that the uPA was cytotoxic for hepatocytes and that inactivation of transgene expression by DNA rearrangement in isolated hepatocytes in Alb-uPA mice was followed by repopulation of the entire liver by cells that no longer produce uPA. Sandgren et al., *Cell* 66: 245–256 (1991). The uPA transgene-expressing hepatocytes were at a selective disadvantage relative to hepatocytes (native or non-native) that were not expressing the transgene. Thus, production of uPA by the liver kills hepatocytes over time, and the gene encoding uPA has been used to impair native liver function and stimulate the repopulation of liver with non-native cells. See Brinster et al., PCT Publication WO 94/02601, and Rhim et al., *Science* 263: 1149–1152 (1994).

There remains a significant need in the art for methods of somatic gene therapy that use the liver for efficient expression of gene product in therapeutically useful quantities and duration. Desirably, these methods should (a) avoid the necessity for surgically removing a large portion of the liver, (b) enhance the yield and recovery of transduced hepatocytes without compromising viability; and (c) be independent of the particular disease being treated. Quite surprisingly, the present invention fulfills these and other related needs.

SUMMARY OF THE INVENTION

Methods and compositions are provided for producing a gene product of interest in the liver of a mammal. In one aspect the ex vivo method comprises transducing native hepatocytes which have been removed from the mammal with a vector which encodes the gene product of interest, and transducing in situ native hepatocytes of the mammal with an adenoviral vector which encodes a molecule that stimulates liver regeneration, such as a hepatotoxin. Preferably the hepatotoxin is uPA, and has been modified to inhibit its secretion from the hepatocyte once expressed by the viral vector. In another embodiment the vector encodes tPA, which stimulates hepatocyte regeneration de novo, apparently without hepatocyte killing. The transduced hepatocytes which have been removed from the mammal are returned to the mammal, and conditions are provided which are conducive to expression of the gene product of interest. Typically the transduced hepatocytes are returned to the patient by infusion through the spleen or portal vasculature, and administration may be single or multiple over a period of 1 to 5 or more days.

In an in vivo aspect of the methods of the invention, a retroviral, pseudotype or adenoviral associated vector is constructed which encodes the gene product of interest and is administered to the mammal in conjunction with a regeneration of the liver induced by an adenoviral vector that encodes the secretion-impaired hepatotoxin such as the modified uPA described herein, or encodes tPA, which stimulates hepatocyte regeneration without acting as a hepatotoxin. This method avoids the need for surgery to remove hepatocytes from the mammal prior to administering the adenovirus vector encoding the hepatotoxin. An additional gene can be included in the vector which encodes the gene product of interest, which additional gene encodes a molecule capable of binding to and inactivating the hepatotoxin encoded by the adenovirus vector.

A wide variety of gene products of interest may be administered to a mammal according to the invention, often to treat or prevent a disease associated with the gene product. For example, the gene product of interest can be an enzyme, hormone, cytokines, antigens, antibodies, clotting factors, anti-sense RNA, regulatory proteins, ribozymes, fusion proteins and the like. The methods can thus be used to supply a therapeutic protein such as Factor VIII, Factor IX, erythropoietin, alpha-1-antitrypsin, insulin, interferons, colony stimulating factor, interleukins, G-CSF, GM-CSF, M-CSF, adenosine deaminase, etc.

In another aspect the invention provides non-human transgenic animals which contain a gene encoding a modified, non-secreted hepatotoxin such as the secretion-impaired uPA.

BRIEF DESCRIPTION OF THE FIGURES

FIG. 1A shows the serum concentrations of uPA, PT and SGPT at different times after Ad.RSV-uPA administration (n=5 per point, vertical lines represent the standard deviation). FIG. 1B shows 3H-thymidine uptake into liver DNA after Ad.RSV-uPA, Ad.RSV-hAAT or partial hepatectomy (n=3 animals per point, and vertical lines represent standard deviations).

FIG. 2A represents partial hepatectomy and LNAlbhAAT infusion 48 hours later; FIGS. 2B–D show the effect of Ad.RSV-uPA and LNAlbhAAT infusion on (B) day 3; (C) days 3, 5 and 7; and (D) days 5, 7 and 9. FIGS. 2E and 2F show results of Ad.RSV-Bgal and LNAlbhAAT infusion on: (E) day 3; (F) days 3, 5 and 7. FIG. 2G shows results with nice infused with LTR-CFIX: 48 hours after partial hepatectomy, solid circles; on days 3, 5 and 7 after Ad.RSV-uPA administration, open circles. Each serum sample was analyzed in at least duplicate. Each line represents an individual animal.

FIGS. 3A–C indicate the (A) uPA cDNA; (B) C-terminal modification; and (C) N-terminal modification.

FIG. 4A and B demonstrate the localization of uPA and modified uPAs in tissue culture cells. CHO cells were transduced with the indicated adenovirus vectors. Supernatants and cell lysates were analyzed for: (FIG. 4A) Antigen levels by ELISA (ng antigen/$1 \times 10^6$ cells for supernatants or cell lysates). (4B) Enzymatic activity expressed as units/$1 \times 10^6$ cells for supernants or lysates. Each experiment was performed in duplicate.

DESCRIPTION OF THE SPECIFIC EMBODIMENTS

Figure 1A:
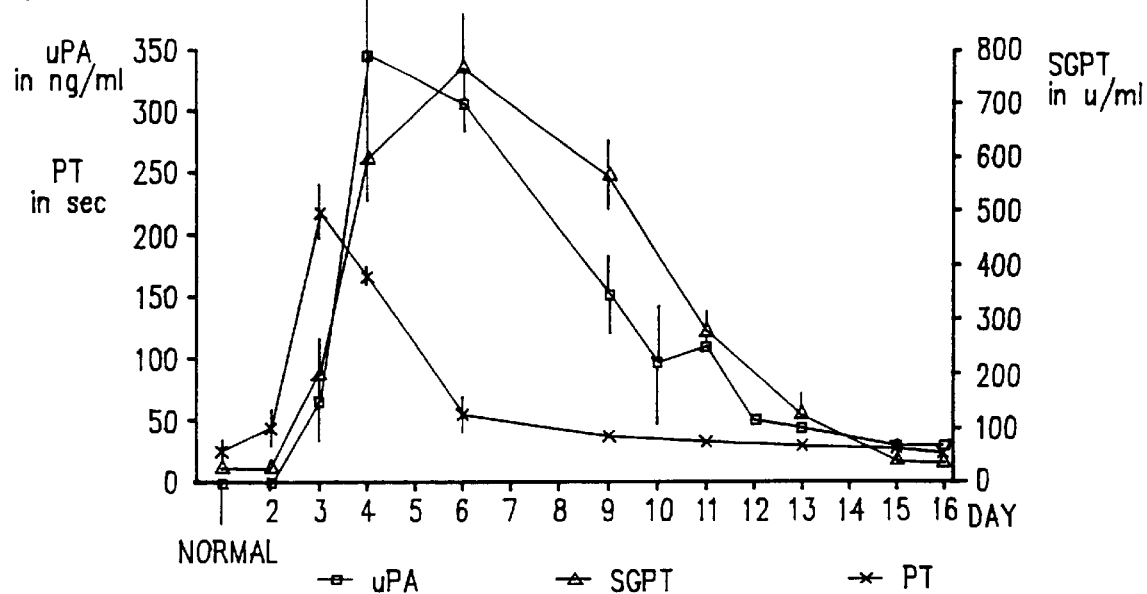
FIG. 1A and FIG. 1B show the effects of Ad.RSV-uPA mediated gene transfer.

The present invention provides methods and compositions for somatic cell gene therapy which is targeted to the liver of a mammal of interest. The gene which is transduced into the hepatocytes of the animal can be expressed in a stable and prolonged manner, thereby providing the animal with an ample supply of gene product to treat or prevent a selected disease.

In one embodiment the invention comprises an ex vivo method of hepatic gene therapy. According to this embodiment a collection of hepatocytes are removed from the individual, typically by surgical or biopsy means. Although a small amount of hepatocytes are necessary, e.g., about $1\times10^7$, sometimes about $1\times10^8$, sometimes about 1 to $5\times10^9$ cells, or up to 20% or more (but desirably less) of the patient's liver can be removed and serve as a source of cellular material for transduction. The hepatocytes are obtained by collagenase liver perfusion and optionally cultured or and prepared for transduction by a vector which contains a gene that expresses the gene product of interest.

The vector can be prepared in any of a wide variety of ways. Typically, the vector will be a retroviral vector and will contain at least one viral long terminal repeat and a promoter sequence upstream of and operably linked to a nucleotide sequence encoding the gene product of interest, followed by at least one viral long terminal repeat and polyadenylation signal downstream of the sequence encoding the gene product of interest. Representative retroviral vectors suitable for use in the present invention are described, for example, in U.S. Pat. Nos. 4,861,719, 5,124,263 and 5,219,740, Kay et al., Hum. Gene Ther. 3: 641–647 (1992) and Kay et al., Science 262: 117–119 (1993), each of which is incorporated herein by reference. Other vectors may also be employed, particularly for the ex vivo methods described herein, such as DNA vectors, pseudotype retroviral vectors, adeno-associated virus, gibbon ape leukemia vector, VSV-G, VL30 vectors, liposome mediated vectors, and the like.

The vector encoding the gene product of interest is used to transduce the hepatocytes which have been isolated from the patient. In some cases, e.g., extreme hepatocellular disease, it may be desirable to use hepatocytes which have been isolated from an individual which is a suitable hepatocyte donor, i.e., one who is substantially the same or closely related in histocompatibility type. The transduced hepatocytes may be cultured for up to 5 to 10 days or longer before being returned to the patient, but typically the cells will be returned to the individual by infusion, typically via the portal or splenic vein, in single or multiple administrations, within 1–5 days after removal.

Prior to reinfusing the transduced hepatocytes to the patient, the patient is infected with an adenoviral vector which encodes a hepatotoxic protein capable of inhibiting or slowly killing hepatocytes. Typically the hepatotoxic protein is one such as urokinase-type plasminogen activator (uPA), or the protein can be tissue-type plasminogen activator (tPA), which can stimulate hepatocyte regeneration de novo, without causing liver damage. The hepatotoxin should be specific for hepatocytes, or if not specific, should not be secreted by the infected hepatocytes into the bloodstream. A representative example is uPA which has been modified by N-terminal and/or C-terminal modifications as described herein so as to inhibit secretion by the infected host cell. In some cases other hepatotoxins may be used, where they are placed under the control of tissue-specific (liver) promoters and are not secreted, or the vectors are specifically targeted to hepatic tissue. These hepatotoxins include the cytotoxic domain of bacterial toxins such as Pseudomonas exotoxin A, diphtheria toxin, cholera toxin, shiga and shiga-like toxin, ribosome inactivating toxins derived from plants and fungi (e.g., ricin), hepatocyte growth factor, and others described in *Genetically Engineered Toxins,* ed. A. Frankel, Marcel Dekker, Inc. (1992), incorporated by reference herein.

Representative adenoviral vectors which can be used to encode the hepatotoxin are described in Stratford-Perricaudet et al., *J. Clin. Invest.* 90: 626–630 (1992), Graham and Prevec, in Methods in Molecular Biology: Gene Transfer and Expression Protocols, 7: 109–128 (1991) and Barr et al., *Gene Therapy,* 2:151–155 (1995), each of which is incorporated herein by reference.

Because the adenovirus is capable of infecting dividing and non-dividing hepatocytes at high efficiency, a sufficient number of adenoviral vector particles should be administered to the liver to infect up to at least about 50% of the hepatocytes, usually about 80%, preferably about 95%, and more preferably 99% to 99.99% or more of the hepatocytes in the individual. In the ex vivo method the adenoviral-hepatotoxin vector is typically administered to the mammal as soon as possible after the hepatocytes have been removed, and prior to or simultaneous with the infusion of the hepatocytes which have been transduced to express the gene product of interest. The adenovirus vector can be administered by a variety of routes, but typically by intravascular infusion via portal vein, and from about 10 up to about 100 or more adenovirus particles per hepatocyte are administered.

The expression of the hepatotoxin encoded by the adenoviral vector can be constitutive or inducible, but typically is constitutive. As the adenovirus-infected hepatocytes which express the hepatocytes die or are inhibited, the hepatocytes which have been treated ex vivo to encode the gene product of interest are returned to the patient. As these cells have not been transduced with the hepatotoxin, they will proliferate and repopulate the liver. Thus, over a period of days to weeks the adenoviral-infected hepatocytes will die and the liver will be regenerated by hepatocytes which encode the gene product of interest.

Expression of the gene encoding the gene product of interest can be constitutive or inducible. If inducible, it will be under the control of a promoter which is different from a promoter which may be used to control expression of the hepatotoxin of the adenoviral vector. A supply of hepatocytes removed from the patient prior to adenoviral infection and which have been transduced by the vector, e.g., retrovirus, can be used to repeat the re-seeding of the liver as necessary. The entire process itself may be repeated as necessary, understanding that an immune response to the adenovirus vector may be generated by repeated administration. The immune response may ameliorate the effect of adenoviral administration and thus necessitate administration of larger quantities of the vector or delivery in a manner by which the particles are shielded from the host's immune system, or the host's immune can be tolerized to the vector.

In another aspect the invention provides for in vivo methods of somatic cell therapy to the liver. According to this method a retroviral, pseudotype or adenoviral associated vector which requires cell division is constructed which encodes the gene product of interest. The vector is administered to the mammal in conjunction with the asynchronous regeneration of the liver which is or has been induced by an adenoviral vector that encodes the non-secreted hepatotoxin such as the modified uPA described herein. This method avoids the need for removing and transducing hepatocytes from the patient prior to administering the adenovirus vector encoding the hepatotoxin.

To increase the percentage of cells which express the gene product of interest in the in vivo method, an additional gene can be included in the vector which encodes the gene product of interest. This additional gene encodes a protein which is capable of binding to the hepatotoxin encoded by the adenovirus vector, and inactivates or inhibits the hepatotoxin's activity. For example, when the hepatotoxin is uPA or tPA the hepatotoxin inhibitor can be plasminogen activator inhibitor I or plasminogen activator inhibitor II.

According to this aspect of the in vivo method, the individual is treated with the adenoviral vector encoding the hepatotoxin as described for the ex vivo approach. The individual is simultaneously or subsequently treated with the retroviral vector encoding the disease-associated gene product of interest and the hepatotoxin inhibitor. Only the retroviral-transduced cells that produce the inhibitor and the disease-associated gene product of interest survive the effects of the hepatotoxin, and these cells selectively repopulate the liver. In yet another aspect the patient is first given a partial hepatectomy, then administered the retrovirus encoding the gene product of interest simultaneously or prior to administration of the adenovirus encoding the hepatotoxin. In each of these methods the resulting liver is comprised of cells which express the disease-associated gene product of interest, thereby preventing or treating the disease in said patient.

As used herein, the terms "treatment" or "treating" cover any treatment of disease, and include: (1) preventing disease from occurring in a subject who does not have the disease or who has not yet been diagnosed as having it; (2) inhibiting or arresting the development of the disease; or (3) regressing or reversing the disease.

According to these methods a wide variety of disease-associated gene products of interest may be employed to treat or prevent the disease of interest. For example, and by way of illustration only, the genes can encode enzymes, hormones, cytokines, antigens, antibodies, clotting factors, anti-sense RNA, regulatory proteins, ribozymes, fusion proteins and the like. The methods can thus be used to supply a therapeutic protein such as Factor VIII, Factor IX, Factor VII, erythropoietin (e.g., U.S. Pat. No. 4,703,008, incorporated herein by reference), alpha-1-antitrypsin, calcitonin, growth hormone, insulin, low density lipoprotein, apolipoprotein E, IL-2 receptor and its antagonists, superoxide dismutase, immune response modifiers, parathyroid hormone, the interferons (IFN alpha, beta, or gamma), nerve growth factors, glucocerebrosidase, colony stimulating factor, interleukins (IL) 1 to 15, granulocyte colony stimulating factor (G-CSF), granulocyte, macrophage-colony stimulating factor (GM-CSF), macrophage-colony stimulating factor (M-CSF), fibroblast growth factor (FGF), platelet-derived growth factor (PDGF), adenosine deaminase, insulin-like growth factors (IGF-1 and IGF-2), megakaryocyte promoting ligand (MPL, or thrombopoietin), etc.

The invention also provides non-human mammals with functioning non-native liver, e.g., human, or native liver which expresses a desired gene product. The animals can be used as models for evaluating a wide variety of disease processes and treatments. For example, the animal models can be used to as models of pathogenesis for infections, e.g., viral infections such as human hepatitis viruses A, B and C, CMV, or the like, or to determine the effectiveness and safety of treatments or vaccines for such infections. The animals also find use for evaluating the treatment and prevention of genetic disorders, e.g., coagulation factor disorders, glycogen storage disease, alpha-1-antitrypsin deficiency, etc.

In one embodiment the non-human animals of the present invention contain a transgene which encodes a modified non-secreted uPA as described herein, e.g., uPA having a modified C-terminus containing KDEL, uPA having the signal peptide on the N-terminus substituted by the RR retention signal and transmembrane region of the type II transmembrane proteins (Schutze et al., *EMBO J.* 13: 1696–1705 (1994); Gorlich et al., *Nature* 357: 47–52 (1992), or a combination of both C-terminal and N-terminal modifications designed to inhibit secretion of the uPA molecule without substantially adversely affecting hepatotoxic activity. Expression of the modified uPA can be under the control of an inducible or constitutive promoter, e.g., the cytochrome P450 promoter of Jones et al., *Nucl. Acids Res.* Simultaneous with or subsequent to expression of the secretion impaired uPA transgene, non-native (e.g., human) hepatocytes are implanted in the transgenic mammal, e.g., a nude or immunodeficient scid mice, to reconstitute the mammal's liver with a large proportion of non-native (e.g., human) hepatocytes. The mammal is then used as a model for ex vivo hepatic gene transfer, or it can serve as a model, for example, of human hepatitis C infection and its treatment, e.g., with ribozymes against hepatitis C viral RNA.

In another embodiment the mammal can be transduced with an adenoviral vector encoding the modified, secretion-impaired uPA and the non-native cells implanted. The mammal's liver is reconstituted with the non-native hepatocytes and the animal used as described above.

In one aspect of the invention, for example, to select ribozymes against hepatitis C, an expression cassette for the ribozyme can be employed where the sequence is embedded in a stable loop region, which in turn is part of an adenoviral va RNA, so that catalytic secondary structure can form independently from the surrounding RNA structures of the expressed RNA. A library of ribozymes with random flanking sequences is cloned into the loop region of the expression cassette. Ribozymes are then selected from the library by the target sequence. Using this method it is possible to isolate an optimal ribozyme which does not only detect accessible cleavage sites within the target RNA, but will also have the optimal structure for allowing efficient cleavage. This permits the simultaneous isolation of several ribozymes directed against different target sites in a particular mRNA and can be adapted to other target RNA by generating sequence specific primers to isolate the respective ribozyme. For example, this method has permitted the selection of a ribozyme against human growth hormone that reduced the hormone mRNA concentration by more than 99% in cell lines expressing stable high levels of the growth hormone mRNA. For reasons of strain variability, ribozymes against HCV RNA preferably are selected against conserved regions of the plus or minus strands of the 5' non-coding region, the core protein, and NS5 RNA polymerase, but RNA of other regions, e.g., env, may also be used. To test for effective ribozymes in cells, HCV cDNA that produces an intact viral RNA is transduced into hepatoma cell lines. Stable, high level expressing clones are isolated and then transfected with the ribozyme expressing cassette. Cleavage of the viral RNA produces a 5'OH group and a 2'–3' cyclic phosphate group producing unstable fragment and decreasing the mRNA concentration within the cell. Ribozyme producing cell lines are compared for the production of HCV RNA. The sequences encoding the selected ribozymes are placed into adenoviral vectors and used to transduce the hepatocytes of the animal of interest, e.g., mice in which the liver has been ablated with the urokinase gene as described herein and reconstituted with human hepatocytes. For example, scid mice that have livers reconstituted with human hepatocytes are infused with hepatitis C particles, or human HCV-infected hepatocytes are used in the reconstitution process. The liver and serum of the animals are monitored for production of virus by quantitative RT-PCR assays. Additionally, immunohistochemical staining of tissues or antigens detection in the blood can be performed. The ribozyme adenovirus is delivered to the animals and efficacy of HCV inhibition determined.

The following Examples are offered by way of illustration, not limitation.

EXAMPLE I

To induce liver regeneration, a recombinant adenoviral vector that expresses human urokinase from the RSV-LTR promoter, Ad.RSV-uPA was constructed. Human uPA can activate plasminogen across species (Wohl et al., *Biochim. Biophys. Acta.* 745:20–31 (1983)).

For construction and production of the recombinant adenoviral vectors, the cDNA for human uPA was obtained from B. Hinzmann (MDC, Berlin) and is described in Nagai et al., *Gene*, 36:183–188 (1985), incorporated herein by reference). The 1.326 kb HindIII/Asp718 uPA fragment that contains the protein coding sequence was inserted into the HindIII/Asp718 sites of pXCJL.1 (Spessot et al., *Virology* 168:378–387 (1989)) under the transcriptional control of the Rous Sarcoma Virus LTR (RSV) promoter, and upstream of the bovine growth hormone polyadenylation signal (Kay et al., *Proc. Natl. Acad. Sci. USA* 91:2353–2357 (1994)). The virus was prepared after co-transfection with pJMI7 (McGrory et al., *Virology* 163:614–617 (1987)) and the vector designated Ad.RSV-uPA.

The screening for Ad.RSV-uPA was carried out by amplification of individual plaques in 293 cells. Three days after infection the supernatant was tested for immunological reactive uPA by ELISA and fibrinolytic activity by fibrin plaque assay (Jespersen et al., *Haemostasis* 13:301–315 (1983)). The last test demonstrated the catalytic activity of uPA produced after Ad.RSVuPA infection.

The construction of viral vector Ad/RSV-hAAT is described in Kay et al., *Hepatology* 21: 815–819 (1995), and the construction of the vector Ad.RSVβGal is described in Stratford-Perricaudet et al., *J. Clin. Invest.* 90:626–630 (1992), incorporated herein by reference. The recombinant viruses were prepared and purified as described in Barr et al., *Gene Therapy* 2:151–155 (1995), incorporated herein by reference. The purified virus was stored in aliquots at −80° C. and freshly diluted with HgDMEM media prior to injection. The viral titers were determined by OD measurements and plaque assay (Graham et al., *Methods in Molecular Biology: Gene transfer and expression protocols* 7:109–128, The Humana Press, (1991)) and ranged from 2 to $5 \times 10^{11}$ pfu/ml. All viral preparations tested negative for the presence of replication competent virus by an assay that can detect 1 wild-type particle per $5 \times 10^5$ pfu of E1 deleted virus (Barr et al., supra).

The construction of the retroviral vectors LTR-cFIX (Kay et al., *Science* 262:117–119 (1993)), LNAlbhAAT and LBgeo (Kay et al., *Hum. Gene Ther.* 3:641–647 (1992)), each of which is incorporated herein by reference, has been described. Recent characterization of the LNAlbhAAT vector showed that a portion of the albumin promoter has been deleted and that a 0.8kb promoter-enhancer fragment remained in the vector. The viruses were titered on 208F cells and the titer for LBgeo (Kay et al., *Hum. Gene Ther.* 3:641–647 (1992)) was $1 \times 10^6$ cfu/ml while the titers for LTR-cFIX (Kay et al., *Science* 262:117–119 (1993)) and LNAlbhAAT were $2 \times 10^6$ cfu/ml. The titer of LNAlbhAAT was about 10-fold less than the original clone used (Kay et al., *Hum. Gene Ther.* 3:641–647 (1992)). Retroviral packaging cell lines were maintained in high glucose DMEM with 10% bovine calf serum (Hyclone). Virus was harvested from confluent packaging lines (in 10 cm dishes) 16 hrs after medium change (5 ml), filtered through a 0.45 μm filter, mixed with polybrene (12 μg/ml) and used immediately for infusion in animals.

C57BL/6 female mice aged 5 to 6 weeks (Jackson Laboratories, Bar Harbor, Me.) were housed in a specific pathogen free environment. Blood samples were obtained by retroorbital bleeding. For portal vein cannulation, mice were anesthetized by an intraperitoneal administration of 0.5 ml of 20 mg/ml 2,2,2-Tribromoethanol. A midline abdominal incision was made and the skin was separated from the peritoneum to create a subcutaneous pocket. The peritoneum was opened and the portal vein was exposed. A silicone tube (0.02" I.D., 0.037" O.D., S/P Medical Grade, Baxter, Ill.) was inserted in the portal vein and perfused with heparinized saline (1 u/ml). An adhesive (Histoacryl Blau, Braun Melsungen AG, Germany) was used to fix the cannula. Thereafter the cannula was tunneled through the peritoneum and secured with a 4.0 silk suture. The 3 cm long cannula was tied off at the distal end and placed subcutaneously in the previously created pocket.

The mice were given the virus no earlier than 24 hrs later. In some mice the portal vein cannulation was performed together with a ⅔ hepatectomy. The partial hepatectomy was carried out according to the procedure described in Kay et al., *Hum. Gene Ther.* 3:641–647 (1992), incorporated herein by reference.

To perfuse the portal vein, mice were anesthetized, the skin was opened at the proximal site of the already existing abdominal incision. The cannula was exposed and connected to a syringe pump. For virus infusion, $0.5 \times 10^{10}$ or $1.0 \times 10^{10}$ pfu of adenovirus (Ad.RSV-uPA, Ad/RSV-hAAT, Ad.RSV-βGal) in 150 μl DMEM were injected over 5 to 10 min into the portal vein through the cannula. Retrovirus perfusion was performed either 48 hr after partial hepatectomy or at different time points (days 3, 5, 7, 9) after adenovirus administration. One ml of filtered retrovirus supernatant with 12 μg/ml of polybrene was infused into the portal vein via the cannula over 50 min with a syringe pump.

All biochemical and histological analysis were performed after injection of $0.5 \times 10^{10}$ pfu adenovirus into the portal vein through the cannula. The ELISA assay for uPA was based on two different monoclonal antibodies directed against the catalytic and receptor-binding domain of uPA. One of the monoclonal antibodies was labelled with peroxidase according to the manufacturer's (Pierce) specifications. The ELISA had a linear range from 1 ng/ml–50 ng/ml. Human α1 antitrypsin (Kay et al., *Hum. Gene Ther.* 3:641–647 (1992)) and cFIX (Kay et al., *Science* 262:117–119 (1993)) concentrations in serum samples were determined by ELISA assay as described. The assays had a linear detection range from 2 to 100 ng/ml. A SIGMA diagnostic kit was used for calorimetric determination of the activity of serum glutamic pyruvic transaminase (SGPT) using 10 μl of serum according to the protocol of the manufacturer (SIGMA procedure: No. 505). Serum total protein and albumin were analyzed by routine automated methods in the clinical pathology laboratories of the University of Washington Hospital, Seattle, Wash. The prothrombin time was determined by a SIGMA Diagnostic kit (Procedure: No. T7280). The test was carried out with 100 μl plasma obtained from citrated blood. The PTs were measured in the presence or absence of 20 μg/ml aprotinin. For $^3$H-thymidine incorporation, the method of Paulsen and Reichelt (Paulsen et al., *Virchow Archiv B Cell Pathology* 62:173–177) was modified. One μCi of 6-$^3$H-Thymidine (5 Ci/mmol, Amersham) in 0.9% saline per gram body weight was injected intraperitoneally 3 times: 24 h, 12 h and 45 min prior to sacrificing the animals. One-third of the liver was fixed in 10% neutral formalin for histological autoradiography. 0.3 g of liver was homogenized in 5 ml 0.2N perchloric acid in a glass Dounce homogenizer on ice and then centrifuged. The pellet was washed once in 5 ml cold 0.2N perchloric acid, once with 5 ml ethanol/ether (1/1, v/v) and once with 2 ml ethanol to remove the acid soluble nucleotides. DNA in the pellet was then hydrolyzed in 5 ml 0.5N perchloric acid at 90° C. for 10 min. Following centrifugation, duplicate aliquots of hydrolyzed DNA were determined for radioactivity. The DNA content in the supernatant was determined by OD reading and by the diphenylamine method (Bucher, *Int. Rev. Cytol.* 15:245–278 (1963)). Specific activity was expressed as cpm/μg DNA.

Infusion of $1 \times 10^{10}$ adenoviral pfu into the portal vein of C57BI/6 mice was known to result in transduction of 100% of hepatocytes with more than 1 copy of adenoviral DNA per cell (Li et al., *Human Gene Ther.* 4:403–409 (1993)). The same dose of Ad.RSV-uPA resulted in 90% mortality that at least in part was related to hemorrhage. When $5 \times 10^9$ pfu of Ad.RSV-uPA was used, the mortality rate was less than 5% and this dose was selected for the majority of the liver regeneration experiments. For comparison, control studies were performed on mice that received the Ad/RSV-hAAT virus or ⅔ partial hepatectomy. After infusion of adenovirus or partial hepatectomy, blood samples were analyzed at different times for serum urokinase concentrations, SGPT (an indicator of hepatocyte damage) and prothrombin time (PT).

The infusion of Ad.RSV-uPA resulted in transient elevations of serum urokinase reaching a peak value of 350 ng/ml (70 to 100 times greater than endogenous levels) four days later before falling to background concentrations by day 12 (FIG. 1A). The rise in uPA was associated with an increase in the serum SGPT concentrations reaching 800 u/ml on day 4 (nl range 20 to 40 u/ml) before slowly falling to normal levels between days 12 to 13. No or minimal elevation in serum SGPT (less than 2-fold greater than normal) was found in Ad/RSV-hAAT treated animals.

Figure 1B:
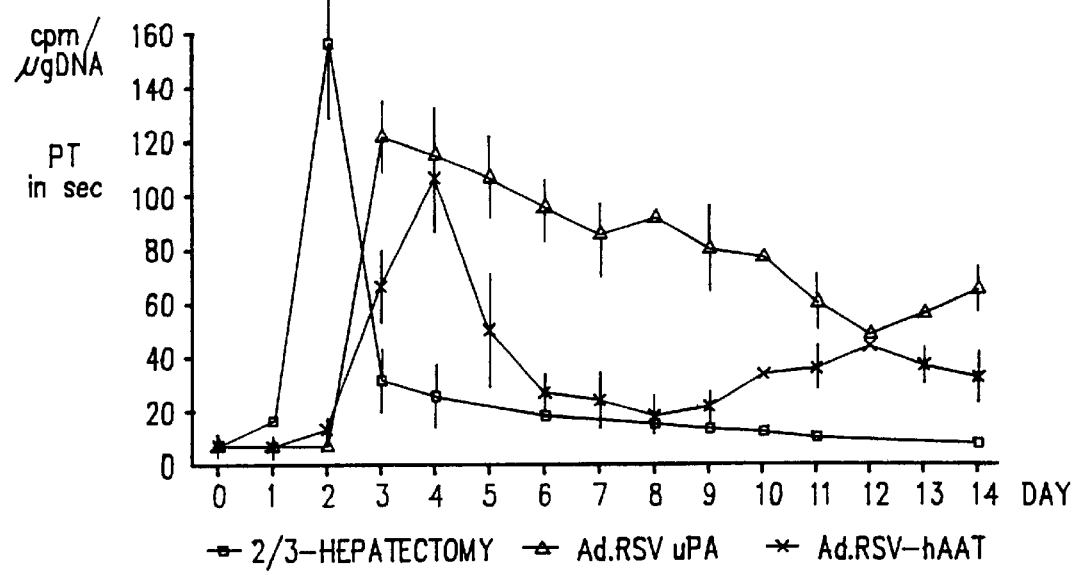

At varying times after adenovirus infusion, animals were infused with $^3$H-thymidine, and the amount of radioactivity incorporated into liver DNA was determined as a means to quantitate cell proliferation (FIG. 1B). In agreement with previous studies (Grundmann et al., in *Liver Regeneration After Experimental Injury,* Lesch & Reuter (eds), Stratton Intercontinental Medical Book Co., New York (1973)), the partial hepatectomized animals had a sharp peak of $^3$H-thymidine uptake 48 hours postoperatively. However, the animals treated with Ad.RSV-uPA had an increased period of $^3$H-thymidine uptake that began on day 3 and persisted for 8 days. Thus, the period of hepatic 3H-thymidine uptake with Ad.RSV-uPA treatment was much greater than that obtained with partial hepatectomy. The recipients of the Ad/RSV-hAAT control adenovirus had a peak of hepatic 3H-thymidine uptake on day 4 that returned to baseline levels 24 h later and a minimal rise in 3H-thymidine uptake on day 11. In total, the hepatic damage as measured by SGPT levels and high rates of 3H-thymidine uptake was attributed to intrahepatic urokinase production.

The PT measured as a means to estimate the coagulation status in Ad.RSV-uPA recipient animals reached more than 200 seconds on day 3 but fell to the normal range between days 11 and 13 (FIG. 1A). Animals which received a partial hepatectomy or control adenovirus had normal PTs. The observed disorders in clotting function in Ad.RSV-uPA transduced mice may have resulted from the elevated serum uPA activity or decreased synthesis of clotting factors by the liver due to hepatocyte degeneration and liver insufficiency. To distinguish between these two possibilities, the PTs were compared in the presence and absence of aprotinin, a plasmin inhibitor. Whereas the PT without aprotinin was 10 times higher than normal (220 sec on day 3) (FIG. 1A), the PT value in the presence of aprotinin was almost normal (35 sec). The high PT without aprotinin likely resulted from active urokinase in the plasma sample that continued to convert plasminogen to active plasmin (and delete fibrin strand formation) in vitro. Thus, Ad.RSV-uPA treated mice did not have a deficiency in clotting factors. Additionally, these animals had normal serum albumin and total protein concentrations. The presence of functional hepatic clotting factors and normal concentrations of serum proteins suggested that significant liver biosynthetic function continued to occur after urokinase induced hepatocellular damage.

For histological analysis liver samples were fixed in 10% neutral formalin, embedded in paraffin and stained with hematoxylin/eosin. The livers of animals that received $1 \times 10^{10}$ pfu of Ad.RSV-uPA (but not Ad/RSV-hAAT) had a white appearance which was observed on days 3 to 7 after adenovirus administration and was similar in gross morphology to that observed in the urokinase transgenic mouse model (Sandgren et al., *Cell* 66:245–256 (1991)). Animals receiving half the dose of adenovirus had an intermediate appearing whitish red liver that was most pronounced around the portal areas. Fourteen days after virus administration the livers appeared normal.

Microscopic histological findings from animals treated with $5 \times 10^9$ pfu of recombinant adenovirus indicated that by day 3, Ad.RSVuPA treated mice had a moderate inflammatory infiltrate that contained macrophages and neutrophils. Degenerative changes in hepatocytes included vacuolization, pyknotic and few mitotic nuclei. By day 4 there was widespread hepatocyte degeneration in about 90% of the hepatocytes. Eight to 10 days after Ad.RSV-uPA administration there was evidence of hepatic recovery including the presence of multifocal regeneration (mostly in the periportal spaces), heterogenous size of nuclei, and a much decreased inflammatory reaction with few degenerating hepatocytes. By three to four weeks, the infiltrate had resolved and the liver appeared normal.

In contrast, the animals receiving the control Ad.RSV-hAAT adenovirus had a mild infiltrate mostly localized to the periportal spaces without evidence of hepatic necrosis and degeneration on days 3 to 6. On days 7 to 9 the liver parenchyma appeared normal but a secondary mild infiltrate was observed on days 11–13 that resolved by day 14. Inflammatory reactions have been observed with adenovirus administration which have been associated with an immunologic response directed against adenoviral transduced cells. This is believed to result from low level production of adenovirus antigens in transduced cells (Yang et al., *Proc. Natl. Acad. Sci. USA* 91:4407–4411 (1994)).

To definitively establish that hepatocytes regenerated after Ad.RSV-upa administration, autoradiography was performed on liver sections obtained from the animals described for FIG. 1. Animals received thymidine injections as described above. Six μm sections were dip-coated with Kodak NTB-2 emulsion diluted 1/1 (v/v) with water, and developed after a 2 week exposure. All slides were counterstained with hematoxylin/eosin. More than 50% of the hepatocyte nuclei from Ad.RSV-uPA treated mice were observed with 3H-label over the period of days 3 to 11 post transduction. The asynchronous DNA replication in different hepatocytes forms the characteristic incorporation curve in FIG. 1B. A few degenerating hepatocytes and non-parenchymal cells were labelled in these sections. The frequency of hepatocyte labelling was about 80% in partial hepatectomized control animals 48 hrs post operatively.

In contrast, the majority of radioactive labelling in Ad/RSV-hAAT treated mice were observed in the inflammatory cells, most of which were localized around the periportal region. These labelled cells were present on days 4 and 11 but were not present in appreciable quantities in between these two time points. Because 3H-thymidine was infused over a 1 day period, it is possible that the inflammatory cells were labelled prior to taking residence in the liver. The presence of labelled inflammatory cells correlated with the amount of radioactive DNA in the liver (FIG. 1). Hepatocyte labelling was detected in the Ad/RSV-hAAT control animals on day 4 but at much reduced levels compared with partial hepatectomized or Ad.RSV-uPA treated animals. Normal untreated mice had rare labelled nuclei. In total, these studies demonstrate that urokinase expression from hepatocytes induced significant liver parenchymal cell regeneration that lasted for a period of 8 days.

The livers from Ad.RSV-uPA treated animals were analyzed for alphafetoprotein (AFP), an oncodevelopmental protein, by immunohistochemical staining. Deparaffinized sections were incubated with a 1:10 dilution of polyclonal rabbit anti-human alpha-fetoprotein antibodies (DAKO) which crossreact with mouse AFP. Specific binding was detected by horseradish peroxidase conjugated goat anti-rabbit antibodies. Human fetal liver was used as a positive control. The results demonstrated that while rare degenerating hepatocytes contained AFP, none of the newly regenerating cells expressed AFP. This indicates that like partial hepatectomy, uPA-induced regeneration occurs by division of mature hepatocytes without dedifferentiation (Fausto, *Curr. Opinion Cell Biol.* 2:1036–1042 (1990)).

EXAMPLE II

Ad.RSV-uPA Treatment Results in Permanent Retroviral-Mediated Gene Transfer In Vivo This Example demonstrates retroviral-mediated gene transfer into the uPA induced regenerating hepatocytes.

Recombinant retrovirus that contained the human α1 antitrypsin cDNA (LNAlbhAAT) was infused (1 ml of $2\times10^6$ pfu) into the portal vein of mice at different times after Ad.RSV-uPA administration. Some mice received multiple infusions of retrovirus. The control animals underwent a partial hepatectomy or were infused with the Ad.RSV-βgal adenovirus in place of Ad.RSV-uPA. The quantity of gene product and the relative hepatic gene transfer rate was determined by periodic measurements of serum HAAT (FIG. 2).

Figure 2A:
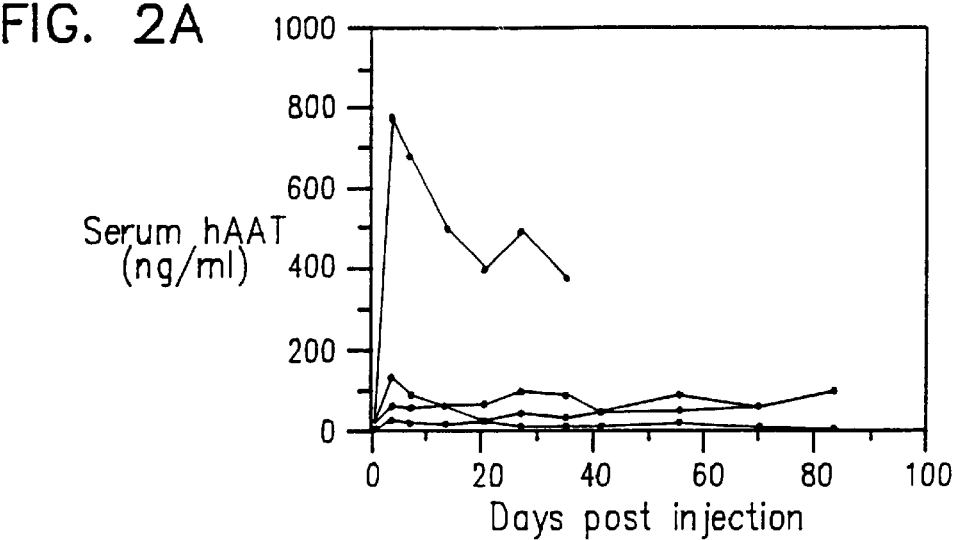
FIGS. 2A–G collectively demonstrate the effect of retrovirus-mediated gene transfer. Mice were subjected to a ⅔ partial hepatectomy or portal vein infusion of $5 \times 10^9$ pfu of recombinant adenovirus on day 0. On varying day(s), the mice were infused (portal vein) with 1 ml of (A–F) LNAlbhAAT or (G) LTR-cFIX retrovirus. Blood samples were periodically analyzed for serum hAAT or cFIX by ELISA.

Partial hepatectomized animals that were injected with LNAlbhAAT retrovirus had constitutive HAAT serum concentrations that varied between 20 to 120 ng/ml in five out of the first six recipients (FIG. 2A). One animal had an unusually high persistent serum HAAT concentration of about 400 ng/ml after partial hepatectomy. To determine whether the high rate of gene transfer observed with partial hepatectomy in the one mouse could be reproduced, six additional mice were treated in a similar manner and all of these animals had serum HAAT concentrations in the 20 to 100 ng/ml range. For partial hepatectomized mice, retroviral-mediated gene transfer only occurred during a small window at about 48 hours (Kay et al., *Hum. Gene Ther.* 3:641–647 (1992)) and multiple infusions of retrovirus after partial hepatectomy did not increase gene transfer.

Figure 2B:
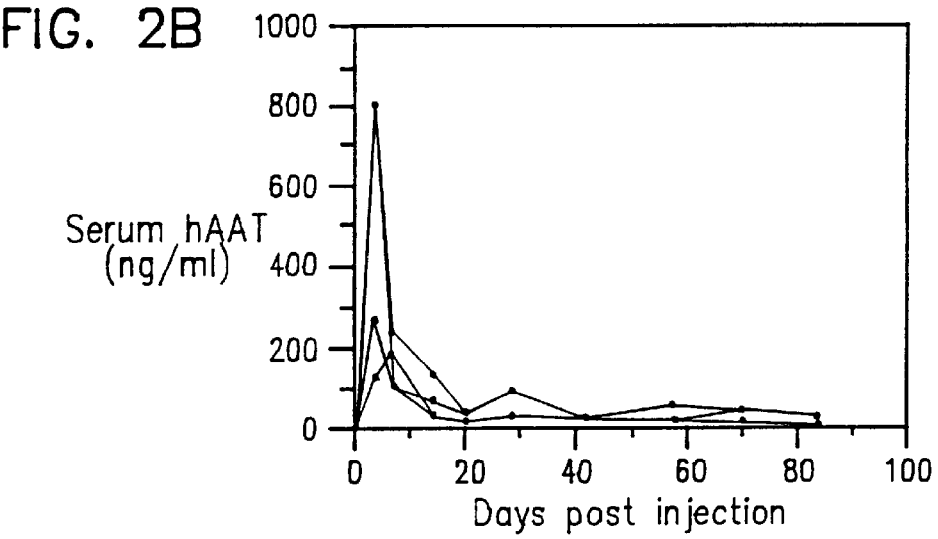

The mice that were infused with a single dose of LNAlbhAAT retrovirus 3 days after Ad.RSV-uPA administration had a high peak of serum HAAT (up to 800 ng/ml) that fell during the first 10 days to constitutive levels ranging from 10 to 100 ng/ml in individual animals (FIG. 2B). The peak level of serum HAAT may have been due to the continued hepatocyte turnover that occurred on days 3 and 4 after Ad.RSV-uPA administration.

Figure 2C:
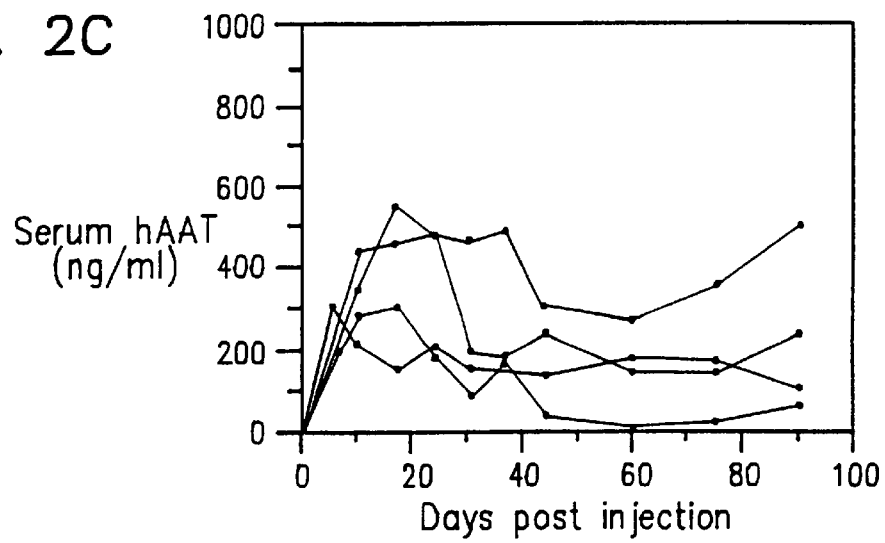
Figure 2D:
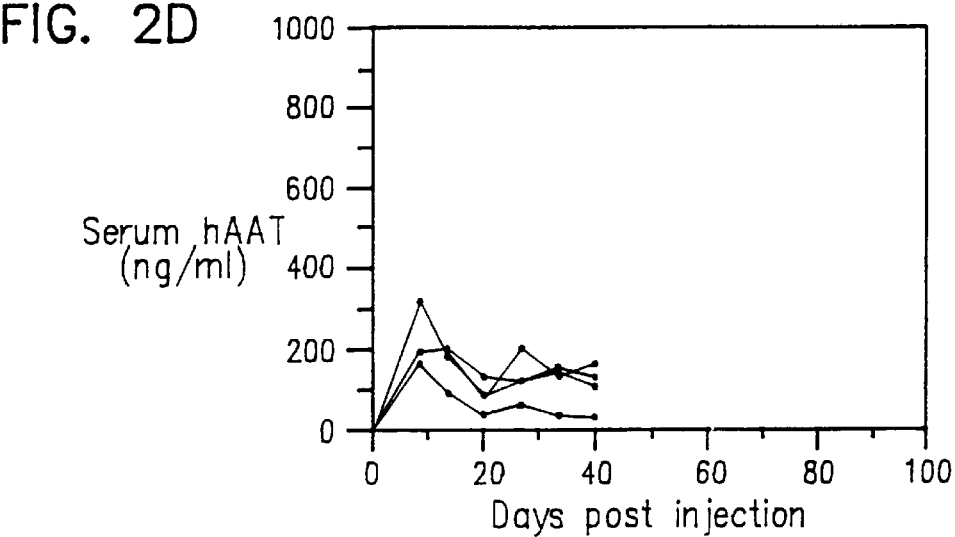
Figure 2E:
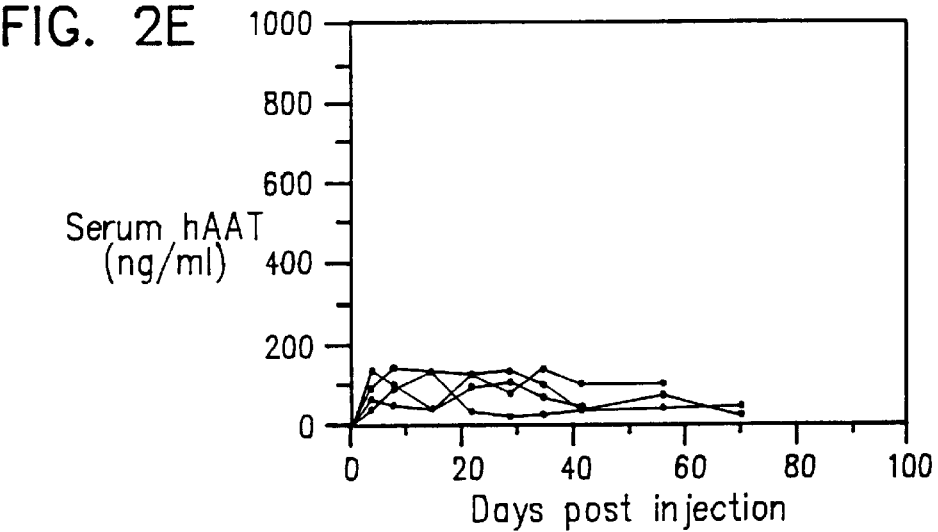
Figure 2F:
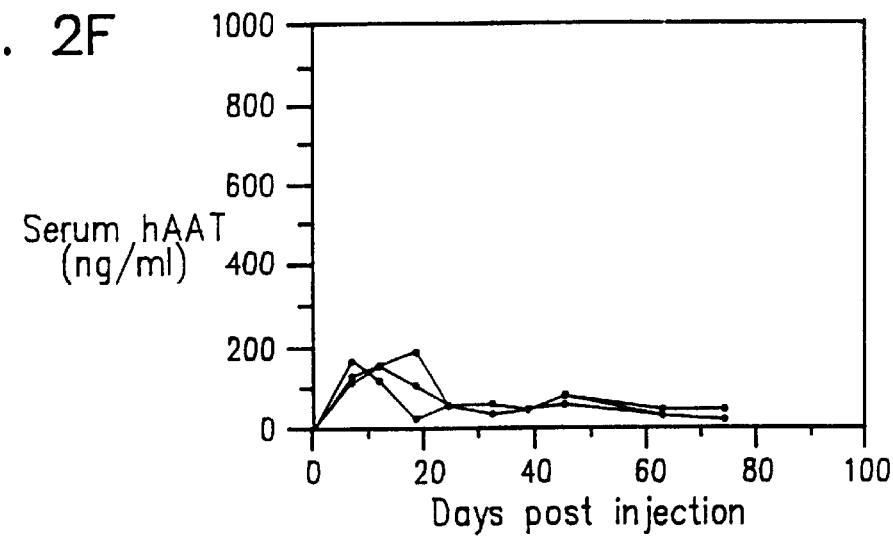
Figure 2G:
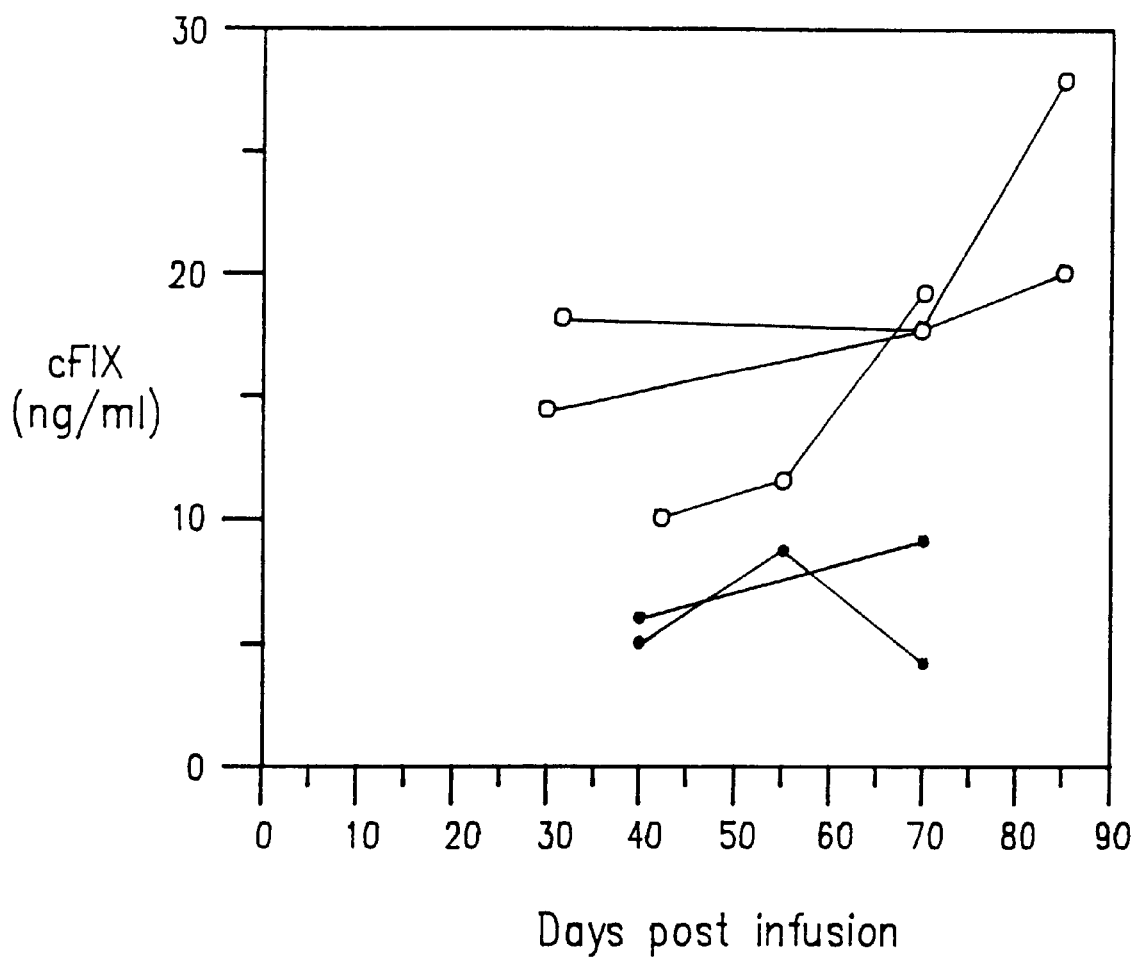

The mice that received three retrovirus (LNAlbhAAT) infusions on days 3, 5 and 7 after Ad.RSV-uPA had constitutive HAAT levels in the 100 to 400 ng/ml range (FIG. 2C). Thus, gene expression as determined by the quantity of the HAAT serum marker was about 5-fold higher using the Ad.RSV-uPA mediated regeneration compared to that obtained with partial hepatectomy. When the retrovirus was infused on days 5, 7 and 9 after Ad.RSV-upa administration, the serum HAAT levels ranged from 100 to 200 ng/m (FIG. 2D). The serum HAAT concentrations from mice that had been infused with a control adenovirus prior to LNAlbhAAT infusion(s) were similar to mice that had received a partial hepatectomy (FIGS. 2E and F). The retrovirus transduction which occurred in mice that received the control adenovirus was likely related to the low level of hepatocyte regeneration. Multiple infusions of LNAlbhAAT after control adenovirus did not lead to an increase in serum concentrations of HAAT (FIG. 2F). Because gene expression was higher in animals given multiple injections, the improved rate of hepatic gene transfer was likely due to the ability to infuse multiple doses of retrovirus.

Figure 4A:
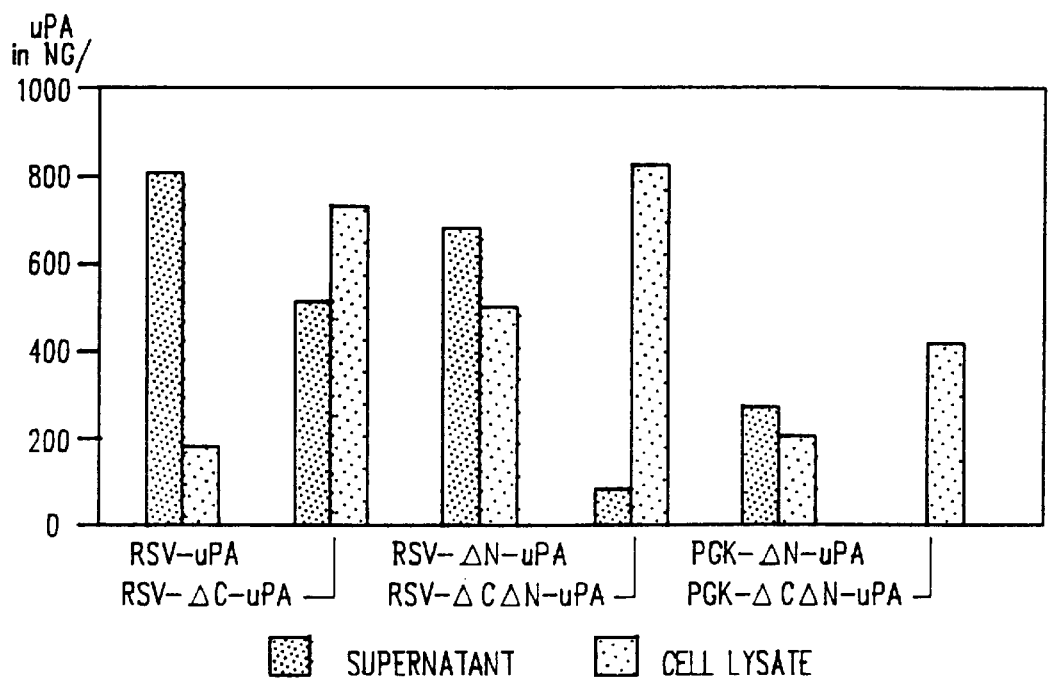
Figure 4B:
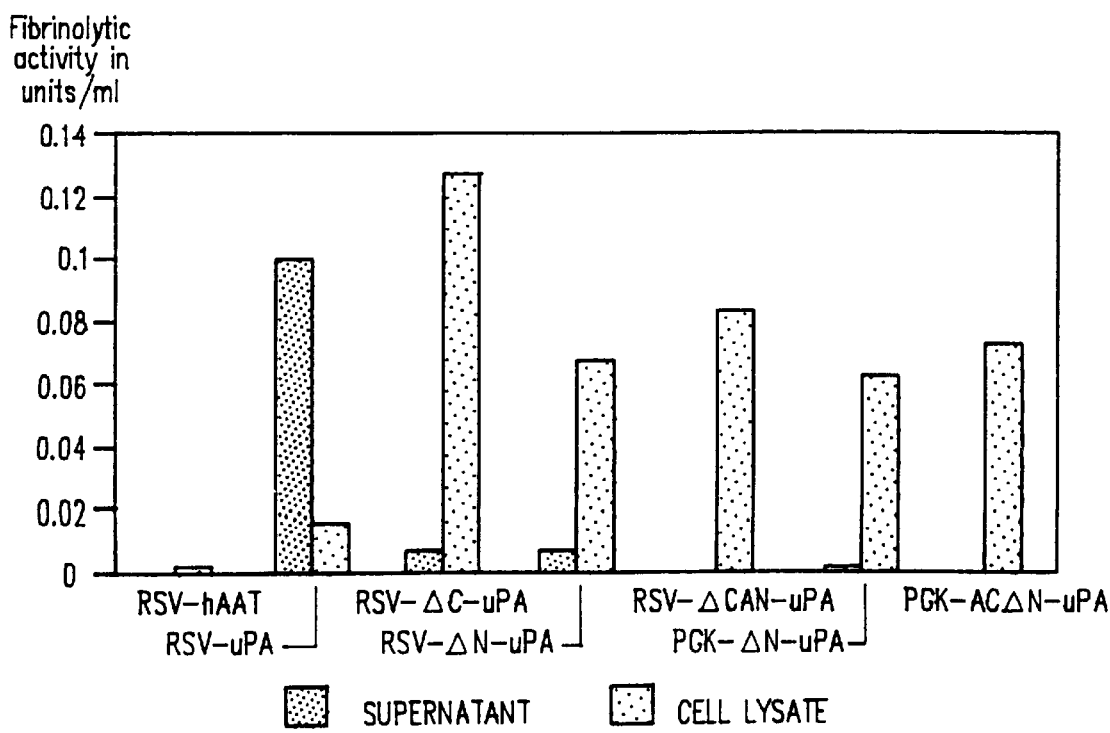

A second recombinant retroviral vector, LTR-cFIX that expresses a therapeutic protein, canine factor IX (Kay et al., *Science* 262:117–119 (1993)) was used to corroborate the findings described above. The data presented in FIG. 4B demonstrated that like HAAT, the serum canine factor IX concentration was several fold higher after Ad.RSV-uPA induced regeneration compared with partial hepatectomy (15–30 ng/ml vs 5–10 ng/ml). Although low, the concentration of cFIX obtained by prokinase induced liver regeneration was greater than that which was obtained in a dog model of hemophilia B (Kay et al., ibid.). The low absolute serum concentration of cFIX may be somewhat misleading because of potential for an altered biological half-life of the canine protein in mice. For example, the biological half-life of human factor VIII and factor IX is reduced by at least 6- and 3-fold respectively when infused in mice (Hoeben et al., *Hum. Gene Ther.* 4:179–186 (1993) and Smith et al., *Nature Genetics* 5:392–402 (1993)).

To establish that gene transfer resulted in hepatocyte transduction, mice that underwent either partial hepatectomy or Ad.RSV-uPA infusion were injected via the portal vein with the LBgeo retroviral vector that expresses *E.coli* beta-galactosidase. Three weeks later, a small portion of the liver was removed for histochemical X-gal staining. From the remaining liver, hepatocytes were isolated, cultured and stained with X-gal. The proportion of blue cells were determined from the population of cultured hepatocytes. For histochemical β-galactosidase analysis, the method was modified as described (MacGregor et al., Humana Press Inc. (1989)). Histochemical analysis for beta-galactosidase activity was performed on thin sliced liver samples that were fixed for 60 min in 4% p-formaldehyde, $0.1M$ $NaH_2PO_4$ pH7.3 at 4° C., then rinsed 3 times for 30 min with $0.1M$ $NaH_2PO_4$, 2 mM $MgCl_2$, 0.01% Na-deoxycholate, 0.02% NP40 and stained overnight at 37° C. with rinsing buffer containing 1 mg/ml X-Gal, 5 mM $K_3Fe(CN)_6$, 5 mM $K_4Fe(CN)_6$ pH7.3. After 24 h postfixation in 10% neutral formalin, the liver was embedded in paraffin, cut, and counterstained with hematoxylin/eosin.

Histochemical X-gal staining of liver sections from Ad.RSV-uPA and LBgeo treated mice, showed some single blue cells and clonal populations of blue cells of up to 6 blue cells per clone while the proportion of βgal positive hepatocytes in culture varied from 7 to 7.5%. This suggests that at least 2 to 3 cell divisions occurred from the time of retrovirus transduction. In partial hepatectomized animals, rare clones of 2 cells were detected and the proportion of βgal positive cells were 0.8%. The transduction efficiencies using the LBgeo vector were in agreement with the relative quantities of hAAT/cFIX using LNAlbhAAT/LTR-cFIX that were seen in FIG. 2 and confirm that retroviral-mediated gene transfer was greater using the urokinase-induced hepatic regeneration compared to partial hepatectomy.

Thus, this Example demonstrates that although this gene transfer strategy caused a transient hepatocellular injury, there was full recovery within a few weeks.

Furthermore, there was no evidence of hepatobiosynthetic deficiencies after Ad.RSV-uPA administration. This is in contrast to homozygous transgenic uPA mice that develop fatal liver insufficiency during the first weeks after birth. The unaffected liver status after Ad.RSV-uPA gene transfer is a substantial advantage of the present invention.

EXAMPLE III

Modification of Urokinase cDNA to Minimize uPA Secretion

To avoid the risk of possible hemorrhage in transduced animals secondary to uPA secretion, this Example describes modifying the gene encoding the uPA protein so that the uPA is retained within the cell.

The methods used to make the modifications of the uPA cDNA to create different ER retention signals are summarized in FIG. 3. A carboxyterminal endoplasmic reticulum retention KDEL amino acid signal was cloned onto the 3' end and referred to as ΔC-uPA (FIG. 3B). A ΔN-uPA modification was produced by substituting the 25 N-terminal amino acids with an RR-retention signal, together with the transmembrane anchor (TM) separated by a 31 amino acid spacer from the membrane II protein Iip 33 (FIG. 3C), thereby deleting the signal peptide. A third construct contained a combination of the N- and C-terminal modifications (ΔNΔC-UPA). Recombinant adenovirus vectors that express the unmodified uPA (Example I) or the modified constructs were prepared from expression cassettes that used the RSV-LTR and/or PGK promoters.

The human uPA cDNA (1326bp) cloned as XbaI/Asp718 fragment in pGEM (Promega) was obtained from B.Hinzmann (MDC Berlin) (Nagai et al., *Gene*, 36:183–188 (1985)). For the modification ΔC-uPA, the 3' end of uPA cDNA was extended by a sequence coding for the KDEL signal with additional upstream residues as depicted in FIG. 3. The additional amino acids were included because some of the acidic residues upstream of the tetrapeptide KDEL may be important for the conformation of this domain or for the interaction with the KDEL receptor (Pelham, *EMBO J.* 7:913–918 (1988)).

The sequence for the modified C-terminus (75nt) was cloned as synthetic oligonucleotide instead of the Bam HI (position:1257)/Asp718 (FIG. 3) fragment of uPA.

The 75nt long ds oligonucleotide was generated by annealing the following phosphorylated ss oligonucleotides (I–V):

*EMBO J.,* 13:1696–1705 (1994); Strubin et al., *Cell* 47:619–625 (1986)) together with the transmembrane anchor (TM) separated by a spacer peptide (31 aa) from the membrane II protein Iip33 (FIG. 3C). The Iip33 fragment was cloned by PCR from the Iip33 cDNA, provided by P. Petersen (R. W. Johnson Pharmaceutical Research Institute, San Diego, Calif.). The forward primer was designed for the Iip33 sequence coding for the Met +1 and following amino acids with a 5' extension containing a XbaI site and a Kozak sequence upstream of the Iip33-ATG:

5'GGCTCTAGATCGCCACC ATG CAC AGG AGG AGA AGC AGG AGC (SEQ ID NO:6)

The reverse primer was specific against the Iip33 sequence coding for aa 68–74 with a 5' extension for the in frame fusion with uPA by a Taq I site at position 108 of the uPA cDNA:

5'GTT CGA TGG AAC CTG CTG CTG CTA CAG GAA GTA GGC (SEQ ID NO:7)

The PCR was carried out from 50 ng Iip33 DNA by Pfu-DNA polymerase (2.5 u) (Stratagene) with 2% DMSO, 300 mM dNTP's, 20 uM of each primer and the Pfu reaction buffer #2 (20 mM Tris-HCl, pH 8.2, 10 mM KCl, 6 mM (NH4)$_2$SO$_4$ 1.5 mM MgCl$_2$, 0.1% Triton X-100) in 40 cycles (45 sec 95 ° C., 45 sec 65 ° C., 90 sec 72° C.) followed by 10 min 72° C. incubation. The amplification product (251 bp) was separated in a 3% NuSieve agarose, purified and digested with TaqI.

A deletion of the uPA 5' end (XbaI/TaqI (pos:108)) was not possible due to multiple TaqI sites within the uPA gene. Thus, a 526 bp Xba I/BalI uPA fragment was first isolated and then recut with TaqI (FIG. 3A). The remaining 421 bp TaqI/BalI fragment was then ligated with the XbaI/TaqI PCR product and the BalI truncated uPA gene/vector. The correctness of the structure of all modifications was confirmed by sequencing from the T7 promoter (ΔC-uPA) and Sp6 promoter (ΔN-uPA) in pGem.

ΔNΔC-uPA was modified at the N-terminus in the same manner as described for uPA. The resulting modified uPA-genes: ΔC-uPA, ΔN-uPA, and ΔNΔC-uPA were cloned as Hind III/Asp718 fragments into the HindIII/Asp718 site of pAdL.1/RSV and pAdL.I/PGK (Fang et al., *Gene Therapy* 1:247–254 (1994), and Kay et al., *Hepatology* 21: 815–819 (1995), incorporated herein by reference).

The resulting adenoviral plasmids were designated:

pAd. RSV—ΔC-uPA pAd. RSV—ΔN-uPA pAd. RSV—ΔNΔC-uPA pAd. PGK—ΔN-uPA pAd. PGK—ΔNΔC-uPA

To generate the E1A-recombinant adenoviruses the plasmids were cotransfected with pJM17 into 293 cells by

```
I:   5'GATCCCGCAGTCACACCAAGGAAGAGAATGGCCTGGCCCCTC   (SEQ ID NO:1)

II:  5'GAAGAAGATACCTCTGAAAAAGATGAGCTCTGAGG           (SEQ ID NO:2)

III: 5'TCTTCCTTGGTGTGACTGCG                          (SEQ ID NO:3)

IV:  5'CAGAGGTATCTTCGAGGGCCAGGCCATTC                 (SEQ ID NO:4)

V:   5'GTACCCTCAGAGCTCATCTTTTT                       (SEQ ID NO:5)
```

For the ΔN-uPA modification the 25 N-terminal amino acids, including the pre-uPA signal peptide, was substituted by the N-terminal RR-retention signal (Schutze et al., calcium phosphate coprecipitation and plaques were isolated as described in Lieber et al., *Hum. Gene Ther.* 6: 5–11 (1995), incorporated herein by reference. Virus from positive plaques was expanded, purified by CsCl ultracentrifugation and titered by OD measuring and plaque assay. The supernatant and cell lysate from 10 plaques of each adenovirus were analyzed for uPA in supernatant and cell lysate by ELISA. To generate cell lysate for ELISA analysis an equal number of cells from 12 well plates was pelleted, resuspended in 10 mM Tris-Cl pH 7.5, incubated in ice for 10 min, and homogenized in a glass Dounce homogenizer (20 strokes). NaCl was added to a final concentration of 137 mM. The ELISA was as described in Example I above, using monoclonal antibodies against the catalytic and receptor-binding domains of uPA.

To determine how much of the modified uPA protein was localized in the cell or secreted into media, Chinese Hamster Ovary cells were transduced with enough adenovirus to transduce most of the cells (Examples I and II). Two days later the supernatants and cell lysates were analyzed for uPA antigen by ELISA (FIG. 4A) and enzyme activity by fibrin plaque (FIG. 4B) assays. The procedures for the fibrin plaque assay were modified from those described by Jespersen and Astrup (1983). Fifteen milligrams of fibrinogen were dissolved in 50 mM Tris-HCl, 140 mM NaCl pH7.5 (TBS) and mixed with 2% Agar Noble in TBS, 25 mM $CaCl_2$, 12.5 mM $MgCl_2$ at 58–60° C. Five micrograms plasminogen and 60 units thrombin were quickly added to the agar-fibrinogen mix and plated out (thickness 5 mm). Fibrin as the product of fibrinogen activation forms polymers which are visible in the agar as cloudy background. Twenty microliter samples or uPA standard dilutions (Sigma) were added in wells with 4 mm diameter and incubated for 4 hr in a humidified chamber. After the diffusion in agar, the uPA forms clear plaques around the cavities. The plaque diameter was measured and the fibrinolytic activity of samples in units/ml was estimated based on a standard curve.

For enzymatic analysis of cell lysates, the cell pellets were resuspended in 0.14M NaCl, 1 mM $MgCl_2$, 10 mM Tris-HCl, pH8.5, 0.5% NP40 and incubated on ice for 20 min.

The results showed that the majority of the unmodified urokinase antigen and enzymatic activity was secreted into the media while all three of the modified uPAs were predominately found in cells. Based on the amount of uPA protein produced from each adenovirus vector, the specific enzymatic activity of the modified uPAs were relatively similar to the wild-type protein. A small proportion of the ΔC-uPA and ΔN-uPA was found in the media, however, there was virtually no detectable uPA protein in the media of double ΔNΔC-uPA modified protein. Thus, the double modified construct was used in the subsequent studies. The total amount of uPA production was slightly greater when the RSV-LTR promoter was used compared with the PGK promoter (FIG. 4).

EXAMPLE IV

Modified uPA Causes Hepatocellular Damage Without Secretion into the Bloodstream This Example demonstrates that Ad.PGKΔNΔC-uPA can be delivered to mouse hepatocytes in vivo and the resulting ΔNΔC-uPA retained in the hepatocytes, causing hepatocellular damage without secretion of uPA protein into the bloodstream or detectable alterations in hemostasis of the treated animal.

Figure 5:
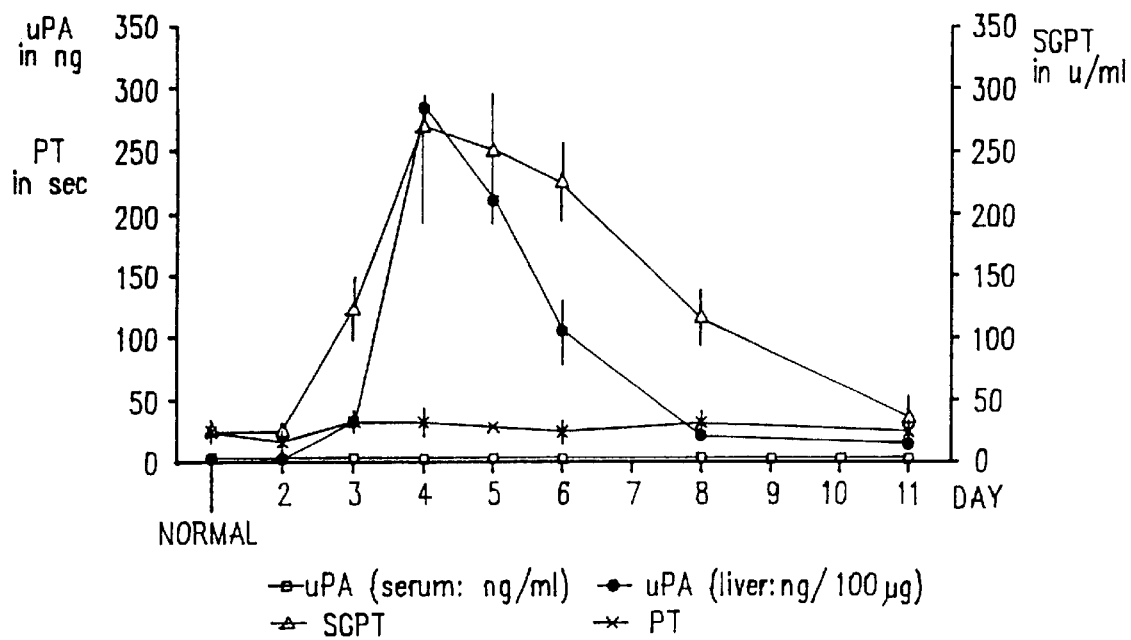
FIG. 5 illustrates measurements of serum SGPT, prothrombin times (PT), uPA antigen in liver and serum from mice given $5 \times 10^9$ pfu of Ad.PGKΔNΔC-uPA adenovirus by portal vein infusion. The vertical bars represent the standard deviation.

Ad.PGKΔNΔC-uPA virus was infused into the portal vein of mice and at periodic times as indicated the blood and liver tissue were analyzed for serum uPA (FIG. 5). The results showed that no uPA was detected in the serum of recipient animals over an 11 day period after gene transfer, whereas the protein was detectable at relatively high concentrations in liver tissue on days 3 to 6 after gene transfer. In contrast, in Example I mice infused with a recombinant adenovirus that expressed wild-type uPA had transient serum concentrations of up to 350 ng/ml. In that group, the elevation in the serum urokinase caused a marked increase in the prothrombin time, an indication of hypocoagulability. In this Example, the PTs were found to be in the normal range in animals infused with Ad.PGK-ΔNΔC-uPA (FIG. 5). Furthermore, unlike wild-type uPA, modified uPA expression in hepatocytes did not cause hemorrhage in any of the animals studied. To monitor for hepatocellular injury, serum SGPTs were measured. The elevation in serum SGPT in animals transduced with Ad.PGK-ΔNΔC-uPA was observed between days 3 and 8 after gene transfer (FIG. 5) and indicated that these animals had hepatocellular injury similar to what was previously described with wild-type uPA. Taken together, the modified uPA caused hepatocellular damage without secretion of the protein into the bloodstream or detectable alterations in hemostasis.

As additional evidence that the ΔNΔC-uPA was localized in the cell, animals were transduced with Ad.RSV-uPA or Ad.PGK-ΔNΔC-uPA and liver sections were immunohistochemically stained for uPA. Although both experimental conditions contained the characteristic histologic appearance of degenerating hepatocytes, the uPA staining patterns showed marked differences. Few of the Ad.RSV-uPA transduced cells contained small amounts of cytoplasmic staining for uPA while a large number of the Ad.PGKΔNΔC-uPA transduced cells were stained with a pattern suggestive of a membrane localization. Six days after Ad.PGKΔNΔCuPA adenovirus administration, uPA stained hepatocytes had the characteristic degenerative changes, while the patches of hepatocytes with normal appearance did not stain. This indicates that the normal hepatocytes represent non-transduced regenerating cells.

Figure 6:
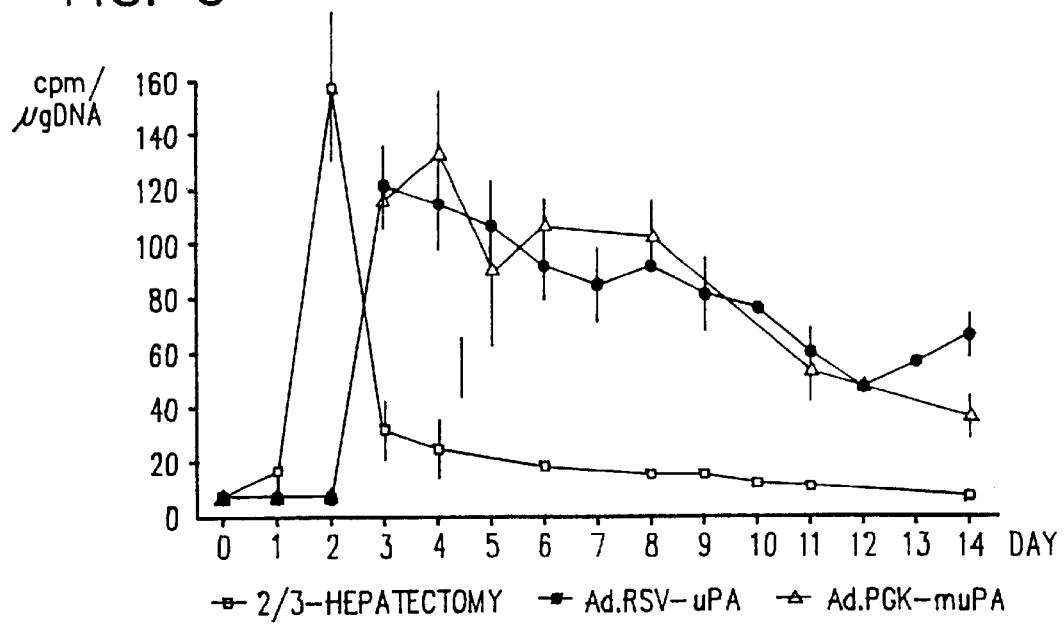
FIG. 6 shows hepatic $^3$H-thymidine uptake. Mice were infused with $5 \times 10^9$ pfu of Ad.PGKΔNΔCuPA adenovirus and at various times the animals were infused with $^3$H-thymidine at 24 h, 12 h and 45 minutes prior to sacrifice. The specific activity was expressed as cpm/μg DNA. The vertical lines represent the standard deviation. At least three animals were analyzed per time point. For comparisons animals receiving partial hepatectomy or Ad.RSV-uPA were included.

To determine whether intracellular production of ΔNΔCuPA caused liver regeneration, animals were infused with either $5\times10^9$ pfu of Ad.RSV-uPA or Ad.PGKΔNΔC-uPA and were analyzed for incorporation of 3H-thymidine into hepatic DNA. Both vectors led to similar rates of radioactive incorporation occurring from days 3 to 11 after gene transfer (FIG. 6). Autoradiography showed that the majority of hepatocytes were labelled with radioactivity. Thus, the ΔNΔCuPA protein produced in hepatocytes caused asynchronous liver regeneration in a manner similar to wild-type uPA.

Figure 7A:
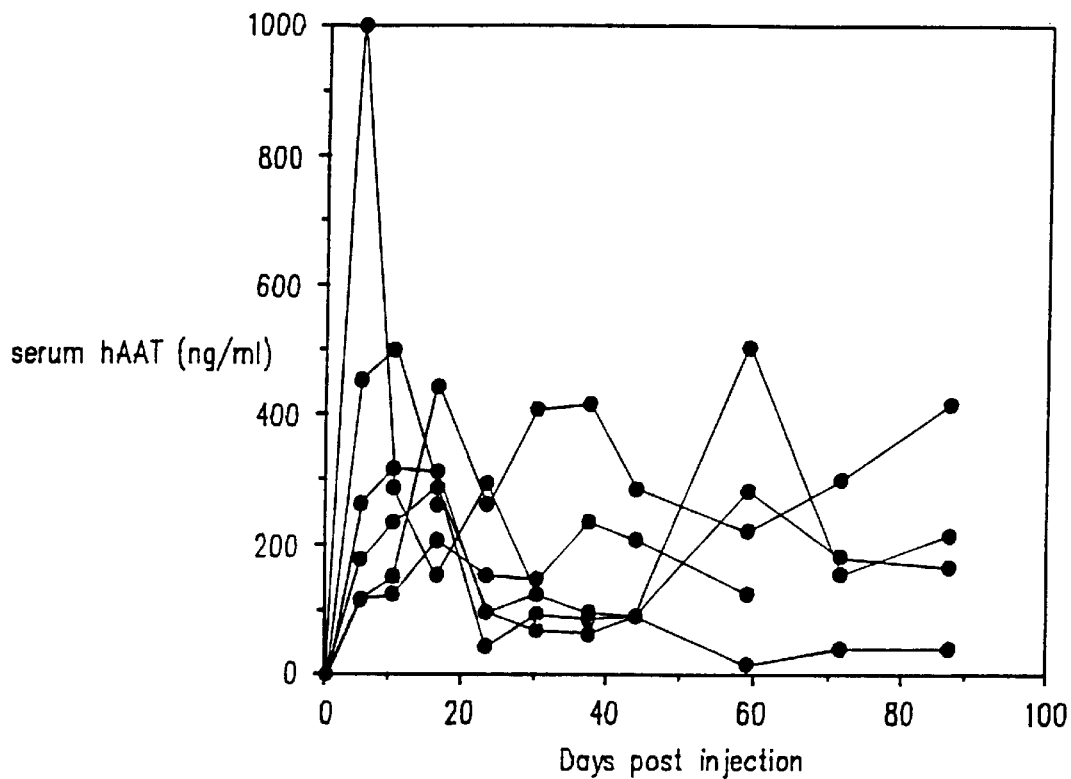
FIGS. 7A and 7B demonstrate results of retrovirus-mediated gene transfer, where mice were infused with $5 \times 10^9$ pfu of (FIG. 7A) Ad.RSV-uPA or (FIG. 7B) Ad.PGKΔNΔC-uPA and 1 ml of LNAlbhAAT ($2 \times 10^6$ cfu) retrovirus on days 3 and 5 after adenovirus infusion. Serum was periodically quantitated for hAAT in at least duplicate. Each line represents an individual animal.
Figure 7B:
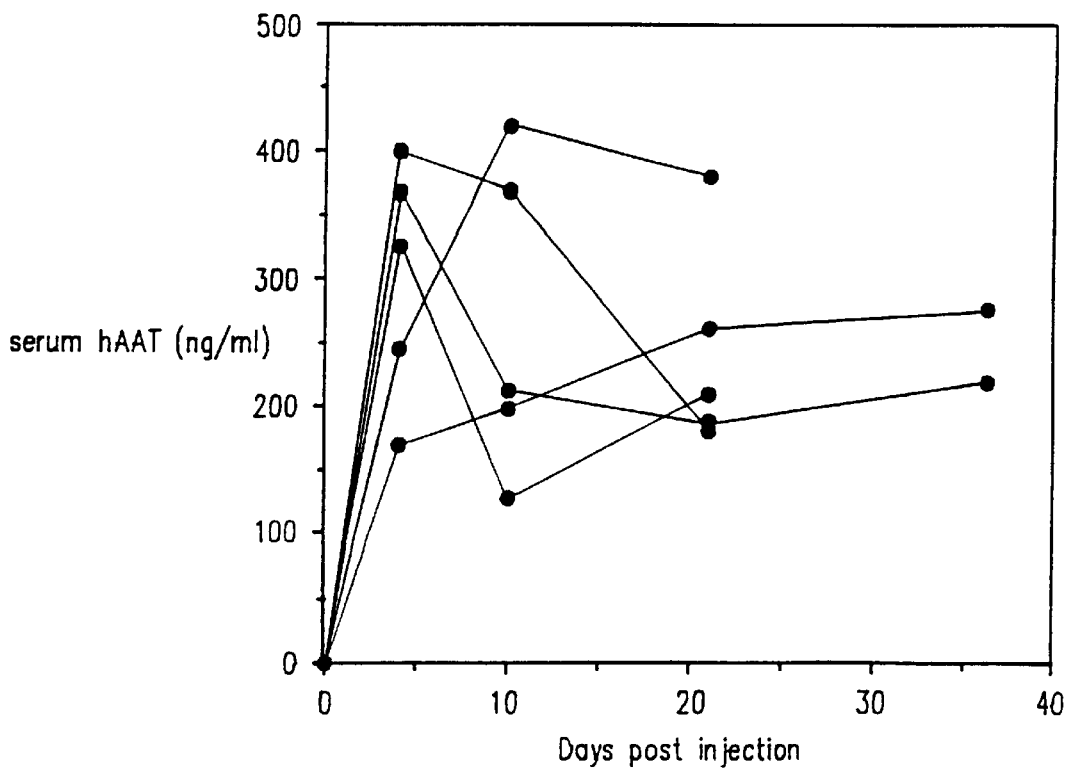

To establish that the Ad.PGKΔNΔCuPA and Ad.RSV-uPA adenovirus treated animals were equally susceptible to retrovirus-mediated gene transfer in hepatocytes in vivo, 3 and 5 days after adenovirus infusion $2\times10^6$ cfu of LNAlb-hAAT retrovirus was infused into the portal vein (FIG. 7). This retrovirus expresses human alpha-1-antitrypsin from transduced cells. The serum hAAT concentrations were similar in both treatment groups, establishing that the new urokinase adenovirus vectors were equally able to allow for retrovirus-mediated hepatic gene transfer.

The results demonstrated herein indicate that both the N- and C-terminal modifications of uPA prevent the secretion of uPA. The KDEL signal seemed to work better in ER retention as the N-terminal modification. The most effective retention of uPA (no detectable secretion) occurred when both termini were modified as with ACANuPA. The pattern of uPA antibody staining in Ad.PGK-ΔNΔC-uPA transduced hepatocytes indicated that the protein is exclusively localized in the ER.

The modified uPA caused similar histologic changes found in a uPA-transgenic mouse model (Sandgren et al., Cell 66:245–256 (1991)), in which ultrastructural examination of the livers showed a characteristic cytoplasmic vacuolization. The vesicles were membrane lined, which contained polyribosomes, suggesting an origin from the rough endoplasmic reticulum. The modified uPA of the present invention was present on similar structures. The presence of modified uPA protein on these vacuolized structures was further evidence that the protein is associated with the endoplasmic reticulum membrane.

EXAMPLE V tPA Causes Hepatocyte Regeneration Without Hepatocyte Killing

Ad.RSV-tpa is an adenovirus vector that contains the 2.7 kb cDNA encoding human tPA under control of the RSV LTR promoter and the bovine plasminogen activator polyadenylation signal, generated in an E1A-deficient adenovirus after recombination with pJM17, as generally described above in Example 3. The tPA is in a secreted form. Ad.RSV-tpa was administered at a concentration of about $5 \times 10^9$ pfu to mice via portal vein injection. Proliferation of hepatocytes was measured by 3H-thymidine incorporation. The Ad.RSV-tpa led to the proliferation of hepatocytes, with peak labeling occurred between days 4 and 5 after adenovirus administration. Three animals per group were analyzed and found to have 90% and 60% hepatocyte labeling on days 4 and 5 respectively. The liver enzymes (SGPT) were in the normal range, and there was no histopathological evidence of hepatocyte injury, in direct contrast to uPA induced liver regeneration. And, whereas Ad.RSV-uPA results in killing of hepatocytes in culture, the Ad.RSV.tPA had no major effects on hepatocytes in culture. As the tPA did not lead to hepatocyte killing prior to regeneration, the stimulus for regeneration is de novo and not the result of a stimulus that resulted from hepatocyte killing.

All publications, patents and foreign patent publications are herein incorporated by reference to the same extent as if each individual publication, patent or patent publication was specifically and individually indicated to be incorporated herein by reference.

Although the foregoing invention has been described in some detail by way of illustration and example for purposes of clarity of understanding, it will be readily apparent that certain changes and modifications may be practiced within the scope of the appended claims.

What is claimed is:

1. A method for producing a gene product of interest in the liver of a patient, comprising:

transducing hepatocytes, which have been removed from said patient, with a vector which encodes the gene product of interest operably linked to a promoter which regulates expression in liver, to produce a transduced population of hepatocytes;

transducing in situ hepatocytes of the patient with an adenoviral vector which encodes tPA or uPA operatively linked to a promoter which regulates expression in liver; and returning the population of transduced hepatocytes to the patient, wherein the gene is expressed and the gene product produced.

2. The method of claim 1, wherein the tPA or uPA is not secreted by the adenoviral-transduced hepatocytes.

3. The method of claim 1, wherein the tPA is secreted by the adenoviral-transduced hepatocytes.

4. The method of claim 1, wherein the gene product of interest is a blood coagulation protein.

5. The method of claim 1, wherein the vector which encodes the gene product of interest is a retroviral vector.

6. The method of claim 1, wherein the transduced population of hepatocytes are returned to the patient by infusion through the spleen or portal vasculature.

7. The method of claim 1, wherein the hepatocytes of the patient are transduced with the adenoviral vector at least 1 to 2 days before the transduced population of hepatocytes are returned to the patient.

8. A method for expressing a gene of interest in hepatocytes of the liver of an individual in need of the gene product encoded by said gene, comprising:

transducing hepatocytes of the individual in situ with an adenoviral vector which encodes tPA or uPA operably linked to a promoter which regulates expression in liver; and transducing hepatocytes of the individual with a vector which contains the gene of interest operably linked to a promoter which regulates expression in liver, whereby the gene of interest is expressed by the hepatocytes of said individual.

9. The method of claim 8, wherein the adenoviral vector encodes human tPA.

10. The method of claim 8, wherein the tPA is secreted by the adenoviral-transduced hepatocytes.

11. The method of claim 8, wherein the vector which encodes the gene product of interest is a retroviral vector.

12. The method of claim 8, wherein the hepatocytes of the patient are transduced with the adenoviral vector at least 1 to 2 days before the hepatocytes are transduced with the vector encoding the gene product of interest.

13. The method of claim 12, wherein the hepatocytes are transduced with the adenoviral vector about 4 days before the hepatocytes are transduced with the vector encoding the gene product of interest.

\* \* \* \* \*

UNITED STATES PATENT AND TRADEMARK OFFICE
CERTIFICATE OF CORRECTION

PATENT NO.    : 5,980,886
DATED         : November 9, 1999
INVENTOR(S)   : Kay et al.

It is certified that error appears in the above-identified patent and that said Letters Patent is hereby corrected as shown below:

Column 4,
Line 27, please delete "nice" and replace therefor with -- mice --.

Column 10,
Line 48, please delete "calorimetric" and replace therefor with -- colorimetric --.

Column 18,
Line 64, please delete "ACANuPA" and replace therefor with -- ΔCΔNuPA --.

Signed and Sealed this

Fifteenth Day of June, 2004

JON W. DUDAS
*Acting Director of the United States Patent and Trademark Office*